US008569460B2

(12) United States Patent
Hansen

(10) Patent No.: US 8,569,460 B2
(45) Date of Patent: Oct. 29, 2013

(54) ANTIBODY CONSTANT DOMAIN REGIONS AND USES THEREOF

(75) Inventor: Geneviève Hansen, Del Mar, CA (US)

(73) Assignee: Vet Therapeutics, Inc., Del Mar, CA (US)

( * ) Notice: Subject to any disclaimer, the term of this patent is extended or adjusted under 35 U.S.C. 154(b) by 724 days.

(21) Appl. No.: 12/660,798

(22) Filed: Mar. 4, 2010

(65) Prior Publication Data
US 2011/0002917 A1 Jan. 6, 2011

Related U.S. Application Data

(60) Provisional application No. 61/163,194, filed on Mar. 25, 2009.

(51) Int. Cl.
C12P 21/08 (2006.01)
(52) U.S. Cl.
USPC .................................... 530/387.3; 530/350
(58) Field of Classification Search
None
See application file for complete search history.

(56) References Cited

U.S. PATENT DOCUMENTS

| | | | | |
|---|---|---|---|---|
| 5,852,183 | A * | 12/1998 | Maeda et al. | 536/23.1 |
| 6,028,059 | A | 2/2000 | Curiel et al. | |
| 6,703,360 | B2 * | 3/2004 | McCall et al. | 514/20.6 |
| 7,531,628 | B2 | 5/2009 | Beall | |
| 8,337,842 | B2 | 12/2012 | Hansen | |
| 2002/0041847 | A1 | 4/2002 | Goldenberg | |
| 2002/0165135 | A1 | 11/2002 | McCall et al. | |
| 2003/0219433 | A1 | 11/2003 | Hansen et al. | |
| 2003/0219861 | A1 | 11/2003 | Rother et al. | |
| 2004/0181039 | A1 | 9/2004 | Krah et al. | |
| 2005/0271662 | A1 | 12/2005 | Beall | |
| 2006/0183195 | A1 | 8/2006 | Lonberg et al. | |
| 2007/0004909 | A1 | 1/2007 | Johnson | |
| 2007/0036799 | A1 * | 2/2007 | Stavenhagen et al. | 424/155.1 |
| 2008/0050370 | A1 | 2/2008 | Glaser et al. | |
| 2008/0188401 | A1 | 8/2008 | Cruwys et al. | |
| 2008/0248529 | A1 | 10/2008 | Carr et al. | |
| 2010/0061988 | A1 | 3/2010 | Hansen | |
| 2011/0002917 | A1 | 1/2011 | Hansen | |
| 2011/0217304 | A1 | 9/2011 | Hansen | |

FOREIGN PATENT DOCUMENTS

| | | |
|---|---|---|
| EP | 0419858 | 4/1991 |
| WO | WO 03/060080 | 7/2003 |
| WO | WO 2004/003019 | 1/2004 |
| WO | WO 2010/027488 | 3/2010 |
| WO | WO 2010/110838 | 9/2010 |
| WO | WO 2011/109108 | 9/2011 |
| WO | WO 2011/109662 | 9/2011 |

OTHER PUBLICATIONS

Adamski, King and Demmer, "Expression of the Fc receptor in the mammary gland during lactation in the marsupial *Trichosurus vulpecula* (brushtail possum)", Mol Immunol 37: 435-444 (2000).
Chaudhury, Mehnaz, Robinson, Hayton, Pearl and Roopenian. et al., "The major histocompatibility complex-related Fc receptor for IgG (FcRn) binds albumin and prolongs its lifespan", The Journal of Experimental Medicine 197: 315-322 (2003).
Cianga, Cianga, Cozma, Ward and Carasevici, "The MHC class I related Fc receptor, FcRn, is expressed in the epithelial cells of the human mammary gland", Hum Immunol 1152-1159 (2003).
Cianga, Medesan, Richardson, Ghetie and Ward, "Identification and function of neonatal Fc receptor in mammary gland of lactating mice," Eur J Immunol 29: 2515-2523 (1999).
Daeron, "Fc receptor biology. Annu Rev Immunol" 5:203-234.
Davis, Dennis, Odom, Gibson, Kimberly, Burrows, and Cooper MD Fc receptor homologs: newest members of a remarkably diverse Fc receptor gene family. Immunol Rev. 190: 123-136 (2002).
Davis, Ehrhardt, Leu, Hirand, Cooper (An extended family of Fc receptor relatives. Eur J Immunol (2005) 35: 674-680.
Fayngerts, Alexander, Najakshin, and Taranin, "Species-specific evolution of the FcR family in endothermic vertebrates." Immunogenetics 59: 493-506 (2007).
Ghetie and Ward, "Multiple roles for the major histocompatibility complex class I- related receptor FcRn", Annu Rev Immunol 18: 739-766 (2000).
Helfand, Hank, Gan and Sondel. Lysis of Human Tumor Cell Lines by Canine Complement plus Monoclonal Antiganglioside Antibodies or Natural Canine Xenoantibodies. Cellular Immunology 167: 99-107 (1996).
Kacskovics, Wu, Simister, Frenyo and Hammarstrom, Cloning and characterization of the bovine MHC class I-like Fc receptor, J Immunol 164: 1889-1897 (2000).
Kim, Bronson, Hayton, Radmacher, Roopenian and Robinson et al., Albumin turnover: FcRn-mediated recycling saves as much albumin from degradation as the liver produces, Am J Physiol Gastrointest Liver Physiol (2005).
Lillieh ̂ ook, Johannisson, and Hakansson. Expression of adhesion and Fcgamma-receptors on canine blood eosinophils and neutrophils studied by anti-human monoclonal antibodies. Vet Immunol Immunopathol. 61: 181-93 (1998).
Maltais Lovering, Taranin, Colonna, Ravetch, Dalla- Favera, Burrows, Cooper, Davis New nomenclature for Fc receptor-like molecules. Nat Immunol 7: 431-432 (2006).
Mayer, Doleschall, Bender, Bartyik, Bosze and Frenyo et al., Expression of the neonatal Fc receptor (FcRn) in the bovine mammary gland,J Dairy Res 72 (Spec No: 107-112) (2005).

(Continued)

Primary Examiner — Brad Duffy
(74) Attorney, Agent, or Firm — Hoxie & Associates LLC

(57) ABSTRACT

The invention provides recombinant protein (e.g., a recombinant antibody or soluble receptor) having (i) a binding domain capable of specific binding to an epitope (for example an antibody variable domains, a receptor, a growth factor, a cytokine, or a fragment of any of the foregoing which is capable of specifically binding the desired epitope) and (ii) an effector domain comprising a constant domain region which is derived from immunoglobulin of a first species which is a companion mammal, e.g. dog, cat, or horse, having engineered substitutions at one or more positions and having an altered interaction with one or more FcRs or other ligands, and optionally enhanced effector function, relative to the parent constant domain region.

14 Claims, No Drawings

(56) References Cited

OTHER PUBLICATIONS

Mayer, Zolnai, Frenyo, Jancsik, Szentirmay and Hammarstrom et al., Localization of the sheep FcRn in the mammary gland, Vet Immunol Immunopathol 87: 327-330 (2002).

Mayer, Zolnai, Frenyo, Jancsik, Szentirmay and Hammarstrom et al., Redistribution of the sheep neonatal Fc receptor in the mammary gland around the time of parturition in ewes and its localization in the small intestine of neonatal lambs, Immunology 107: 288-296 (2002).

Phillips, Padilla, Dickerson, Lindstrom, and Helfand. Immunostimulatory effects of human recombinant interleukin-12 on peripheral blood mononuclear cells from normal dogs. Vet Immunol Immunopathol. 70: 189-201 (1999).

Robinson et al., Albumin turnover: FcRn-mediated recycling saves as much albumin from degradation as the liver produces, Am J Physiol Gastrointest Liver Physiol (2005).

Rodewald, R, pH-dependent binding of immunoglobulins to intestinal cells of the neonatal rat, J Cell Biol. 71: 666-669 (1976).

Sato, Teshima, Nakamura, Takagi, Sasaki, Sawada, and Kitani Canine mast cell activation via human IgG1 and IgG4. Int Arch Allergy Immunol. 135:154-60 (2004).

Schnulle and Hurley, Sequence and expression of the FcRn in the porcine mammary gland, Vet Immunol Immunopathol. (2003) 91: 227-231.

Simister and Mostov an Fc receptor structurally related to MHC class I antigens, Nature 337: 184-187 (1989).

Soergel, MacEwen, Vail, Potter, Sondel, and Helfand. The immunotherapeutic potential of activated canine alveolar macrophages and antitumor monoclonal antibodies in metastatic canine melanoma. J Immunother. 22: 443-53 (1999).

International Search Report and Written Opinion of the International Searching Authority [US] for International Application No. PCT/US2010/00666 mailed Apr. 2, 2012.

Babcock, et al., "Ligand Binding Characteristics of CXCR4 Incorporated into Paramagnetic Proteoliposomes", 276 (42): 3843-38440 (2001).

Brorson et al., "Mutational Analysis of Avidity and Fine Specificity of Anti-Levan Antibodies", (J. Immunol. [1999].

Brummell et al., "Probing the combining site of an anti-carbohydrate antibody by saturation-mutagenesis: role of the heavy-chain CDR3 residues", (Biochemistry [1993] 32: 1180-1187).

Burks et al., "In Vitro scanning saturation mutagenesis of an antibody binding pocket", (PNAS [1997] 94: 412-417).

Caldas et al., (Mol. Immunol. May 2003; 39 (15): 941-952.

Carter et al., "Canine rheumatoid arthritis and inflammatory cytokines" Vet. Immun. Immunopath. 69: 201-214 (1999).

Casset et al., "A Peptide Mimetic of an anti-CD4 Monoclonal Antibody by Rational Design" BBRC [2003] 307: 198-205).

Chabanne, Manuscript available (2006) World Congress WSAVA/FECAWA/CSAWA, reprinted on www.IVIS.org; pp. 456-459.

Chen et al., "Selection and Analysis of an Optimized Anti-VEGF Antibody: Crystal Structure of an Affinity-matured Fab in complex with Antigen", (J. Mol. Bio. [1999] 293, 865-881).

Chien et al. (Proc. Natl. Acad. Sci. USA. Jul. 1989; 86 (14): 5532-5536).

Chun, "Lymphoma: Which Chemotherapy Protocol and Why?", Topics in Companion Animal Medicine, 24 (3): 157-162 (2009).

Colman, "Effects of amino acid sequence changes on antibody-antigen interactions", (Research in Immunol. [1994] 145: 33-36).

Das, et al., Evolutionary Dynamics of the Immunoglobulin Heavy Chain Variable Region Genes in Vertebrates, 60:47-55 (2008).

Das, et al., "Evolutionary Redefinition of Immunoglblulin Light Chain Isotypes in Tetrapods Using Molecular Markers", 105 (43): 16647-16652 (2008).

De Pascalis et al., "Grafting of 'Abbreviated' Complementarity-Determining Regions Containing Specificity-Determining Residues Essential for Ligand Contact to Engineer a Less Immunogenic Humanized Monoclonal Antibody" (The Journal of Immunology [2002] 169: 3076-3084).

Doom et al., "Immunopathological mechanisms in dogs with rupture of the cranial cruciate ligament" 125: 143-161 (2008).

Dutra et al., (Braz. J. Bed. Biol. Res. Nov. 2004; 37 (11): 1673-1681).

Ferrer, L., "Canine Atopic Dermatitis: Evidence Based Dermatology", Proceeding of the NAVC North American Veterinary Conference, Jan 8-12, Orlando, FL. (2005).

Gershwin, L., Veterinary Autoimmunity: Autoimmune Diseases in Domestic Animals:, Ann. N.Y. Acad. Sci. 1109: 109-116 (2007).

Giusti et al. (Proc. Natl. Acad. Sci. USA. May 1987; 84 (9); 2926-2930).

Gussow et al. (Methods in Enzymology. 1991; 203:99-21).

Hale, et al., "CD52 (CAMPATH-1)" J. Biol. Regul. Homeost. Agents 15: 386-391 (2001).

Holm et al., "Functional Mapping and Single Chain Construction of the Anti-Cytokeratin 8 Monoclonal Antibody TS1", (Mol. Immunol. [2007] 44: 1075-1084).

Jang et al., "The structural basis for DNA binding by an anti-DNA autoantibody", (Molec. Immunol. [1998] 35: 1207-1217).

Jubala et al. "CD20 Expression in Normal Canine B Cells and in Canine non-Hodgkin Lymphoma", Vet. Pathol. 42: 468-476 (2005).

Kano et al., "Canine CD20 gene" Vet. Imm Immunopath. 108: 265-268 (2005).

Kobayashi et al., "Trytophan H33 plays an important role in pyrimidine (6-4) pyrimidine photoproduct binding by a high-affinity antibody" (Protein Engineering [1999] 12: 879-844).

Kumar et al., "Molecular Cloning and Expression of the Fabs of Human Autoantibodies in *Escherichia coli*", (J. Biol. Chem. [2000] 275: 35129-35136).

Maccallum et al., "Antibody-antigen interactions: Contact Analysis and Binding Site Topography" (J. Mol. Biol. [1996] 262: 732-745).

Maccoux, L.J., et al. "Expression profiling of select cytokines in canine osteoarthritis tissues" Vet. Immun Immunopath. 118: 59-67 (2007).

Mariuzza, et al., (Annu. Rev. Biophys. Biophys. Chem. 1987; 16: 139-159.

Mayer, Zolnai, Frenyo, Jancsik, Szentirmay, and Hammarstrom et al., Redistribution of the sheep neonatal Fc receptor in the mammary gland around the time of parturition in ewes and its localization in the small intestine of neonatal lambs, Immunology 107: 288-296 (2002).

Mazza et al. "The Separation and Identification by Monoclonal Antibodies of Dog IgG Fractions", J. Imm. Meth. 161: 193-203 (1993).

Mazza, et al. "Tissue Immunoglobulin G Subclasses Observed in Immune-mediated Dermatopathy, Deep Pyoderma and Hypersensitivity Dermatitis in Dogs", Vet. Sci. 58: 82-89 (1995).

Mirzabekov et al., "Paramagnetic Proeteoliposomes Containing a Pure Native, and Oreiented Seven-Transmembrane Segment Protein, CCR5", Nat. Biotech. 18: 649-654 (2000).

Paul, Fundamental Immunology, 3$^{rd}$ Edition, 1993, pp. 292-295.

R&D Systems product literature for antibody AF2305 dated Jun. 9, 2006 and accessed Jun. 5, 2012.

R&D Systems product literature for antibody MAB16091 dated Jan. 24, 2005 and accessed Jun. 5, 2012.

Ravetch and Kinet "Fc Receptors." Annu Rev Immunol 9: 457-492 (1991).

Rudikoff et al. (Proc. Nat'l. Acad. Sci. USA vol. 79, pp. 1979-1983(1982).

Shin et al., "Studies of cocktail therapy with multiple cytokines for neoplasia or infectious disease of the dog I. cDNA cloning of canine IL-3 and IL-6", J. Vet. Sci. 2 (2): 115-120 (2001).

Smith-Gill et al., "Contributions of immunoglobulin heavy and light chains to antibody specificity for lysozyme and two haptens", (J. Immunol. [1987] 139: 4135-4144).

Song et al., "Light Chain of Natural Antibody Plays a Dominant Role in Protein Antigen Binding", (Biochem. Biophys. Res. Comm. [2000] 268: 390-394).

Sutton, et al., "The contribution of synovium, synovial derived inflammatory cytokines and neuropeptides to the pathogenesis of osteoarthritis", Vet. J. 179: 10-24 (2009).

Tang et al., "Cloning and Characterization of cDNAs Encoding Four Different Canine Immunoglobulin Gamma Chains" Vet. Imm. Immunopath. 80:259-270 (2001).

Vajdos et al., "Comprehensive Functional Maps of the Antigen-binding Site of an Anti-ErbB2 Antibody Obtained with Shotgun Scanning Mutagenesis", (J. Mol. Biol. [2002] 320, 415-428).

(56) References Cited

OTHER PUBLICATIONS

Ward et al., "Binding activities of a repertoire of single immunoglobulin variable domains secreted from *Escherichia coli*", (Nature [1989] 341: 544-546).

Wilkerson et al., "Lineage Differentiation of Canine Lymphoma/Leukemia's and aberrant Expression of CD Molecules", Vet. Imm. and Immunopath. 106 (3-4): 179-196 (2005).

Winkler et al., (J. Immunol. Oct. 15, 2000; 165 (8): 4505-4514).

Withrow and Macewan'S, "Small Animal Clinical Oncology" (Ed. 4), D. Vail and S. Winthrow, Ed.s, Saunders Elsevier, St. Louis, (2007), Bibliographic Information.

Wozna et al., "The immunological. biochemical and molecular bases of canine senescence and carcinogenesis: a review", Veterinarni Medicina, 57 (7): 350-359 (2012).

Wu et al., "Humanization of a Murine Monoclonal Antibody by Simultaneous Optimization of Framework and CDR Residues", (J. Mol. Biol. [1999] 294, 151-162).

Written Opinion of the International Searching Authority for International Application No. PCT/US2009/004997 mailed Feb. 17, 2010.

Extended European Search Report Issued Dec. 21, 2012 for EP application 09811845.8 (PCT/US2009004997).

GenBank Direct Submission AAL35304.1; Immunoglobulin Gamma Heavy Chain D [Canis lupus familiaris]; Nov. 26, 2011; ,http://www.ncbi.nm/nih.gov/protein/AAL35304.1>.

International Search Report and Written Opinion of the International Searching Authority for International Application No. PCT/US2011/027094 mailed May 4, 2011.

UniProtKB Direct Submission QT8896. CD52_CANFA; Feb. 1, 1998; >http://www.ncbi.nlm.nih.gov/protein/3182945?sat=OLID&satkey=5321424>.

\* cited by examiner

```
                              SEQUENCE LISTING

<160> NUMBER OF SEQ ID NOS: 25

<210> SEQ ID NO 1
<211> LENGTH: 333
<212> TYPE: PRT
<213> ORGANISM: Canis

<400> SEQUENCE: 1

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Ile Pro Glu Pro Val Thr Val Ser Trp Asn Ser Gly Ser Leu Thr Ser
        35                  40                  45

Gly Val His Thr Phe Pro Ser Ile Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Thr Asn Thr Lys Val Asp Lys
                85                  90                  95

Pro Val Val Lys Glu Cys Glu Cys Lys Cys Asn Cys Asn Asn Cys Pro
            100                 105                 110

Cys Pro Gly Cys Gly Leu Leu Gly Gly Pro Ser Val Phe Ile Phe Pro
        115                 120                 125

Pro Lys Pro Lys Asp Ile Leu Val Thr Ala Arg Thr Pro Thr Val Thr
    130                 135                 140

Cys Val Val Val Asp Leu Asp Pro Glu Asn Pro Glu Val Gln Ile Ser
145                 150                 155                 160

Trp Phe Val Asp Ser Lys Gln Val Gln Thr Ala Asn Thr Gln Pro Arg
                165                 170                 175

Glu Glu Gln Ser Asn Gly Thr Tyr Arg Val Val Ser Val Leu Pro Ile
            180                 185                 190

Gly His Gln Asp Trp Leu Ser Gly Lys Gln Phe Lys Cys Lys Val Asn
        195                 200                 205

Asn Lys Ala Leu Pro Ser Pro Ile Glu Glu Ile Ile Ser Lys Thr Pro
    210                 215                 220

Gly Gln Ala His Gln Pro Asn Val Tyr Val Leu Pro Pro Ser Arg Asp
225                 230                 235                 240

Glu Met Ser Lys Asn Thr Val Thr Leu Thr Cys Leu Val Lys Asp Phe
                245                 250                 255

Phe Pro Pro Glu Ile Asp Val Glu Trp Gln Ser Asn Gly Gln Gln Glu
            260                 265                 270

Pro Glu Ser Lys Tyr Arg Met Thr Pro Pro Gln Leu Asp Glu Asp Gly
        275                 280                 285

Ser Tyr Phe Leu Tyr Ser Lys Leu Ser Val Asp Lys Ser Arg Trp Gln
    290                 295                 300

Arg Gly Asp Thr Phe Ile Cys Ala Val Met His Glu Ala Leu His Asn
305                 310                 315                 320

His Tyr Thr Gln Lys Ser Leu Ser His Ser Pro Gly Lys
                325                 330
```

<210> SEQ ID NO 2
<211> LENGTH: 335
<212> TYPE: PRT
<213> ORGANISM: Canis

<400> SEQUENCE: 2

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Phe Pro Glu Pro Val Thr Val Ser Trp Asn Ser Gly Ser Leu Thr Ser
        35                  40                  45

Gly Val His Thr Phe Pro Ser Val Leu Gln Ser Ser Gly Leu Tyr Ser
    50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 3
<211> LENGTH: 335
<212> TYPE: PRT
<213> ORGANISM: Canis

<400> SEQUENCE: 3

Ala Ser Thr Thr Ala Pro Ser Val Phe Pro Leu Ala Pro Ser Cys Gly

```
1               5               10              15
Ser Thr Ser Gly Ser Thr Val Ala Leu Ala Cys Leu Val Ser Gly Tyr
            20              25              30

Phe Pro Glu Pro Val Thr Val Ser Trp Asn Ser Gly Ser Leu Thr Ser
            35              40              45

Gly Val His Thr Phe Pro Ser Val Leu Gln Ser Ser Gly Leu Tyr Ser
            50              55              60

Leu Ser Ser Met Val Thr Val Pro Ser Ser Arg Trp Pro Ser Glu Thr
65              70              75              80

Phe Thr Cys Asn Val Ala His Pro Ala Ser Lys Thr Lys Val Asp Lys
            85              90              95

Pro Val Pro Lys Arg Glu Asn Gly Arg Val Pro Arg Pro Pro Asp Cys
            100             105             110

Pro Lys Cys Pro Ala Pro Glu Met Leu Gly Gly Pro Ser Val Phe Ile
            115             120             125

Phe Pro Pro Lys Pro Lys Asp Thr Leu Leu Ile Ala Arg Thr Pro Glu
            130             135             140

Val Thr Cys Val Val Val Asp Leu Asp Pro Glu Asp Pro Glu Val Gln
145             150             155             160

Ile Ser Trp Phe Val Asp Gly Lys Gln Met Gln Thr Ala Lys Thr Gln
                165             170             175

Pro Arg Glu Glu Gln Phe Asn Gly Thr Tyr Arg Val Val Ser Val Leu
            180             185             190

Pro Ile Gly His Gln Asp Trp Leu Lys Gly Lys Gln Phe Thr Cys Lys
            195             200             205

Val Asn Asn Lys Ala Leu Pro Ser Pro Ile Glu Arg Thr Ile Ser Lys
            210             215             220

Ala Arg Gly Gln Ala His Gln Pro Ser Val Tyr Val Leu Pro Pro Ser
225             230             235             240

Arg Glu Glu Leu Ser Lys Asn Thr Val Ser Leu Thr Cys Leu Ile Lys
                245             250             255

Asp Phe Phe Pro Pro Asp Ile Asp Val Glu Trp Gln Ser Asn Gly Gln
            260             265             270

Gln Glu Pro Glu Ser Lys Tyr Arg Thr Thr Pro Pro Gln Leu Asp Glu
            275             280             285

Asp Gly Ser Tyr Phe Leu Tyr Ser Lys Leu Ser Val Asp Lys Ser Arg
            290             295             300

Trp Gln Arg Gly Asp Thr Phe Ile Cys Ala Val Met His Glu Ala Leu
305             310             315             320

His Asn His Tyr Thr Gln Lys Ser Leu Ser His Ser Pro Gly Lys
                325             330             335

<210> SEQ ID NO 4
<211> LENGTH: 335
<212> TYPE: PRT
<213> ORGANISM: Canis

<400> SEQUENCE: 4

Ala Ser Thr Thr Ala Pro Ser Val Phe Pro Leu Ala Pro Ser Cys Gly
1               5               10              15

Ser Thr Ser Gly Ser Thr Val Ala Leu Ala Cys Leu Val Ser Gly Tyr
            20              25              30

Phe Pro Glu Pro Val Thr Val Ser Trp Asn Ser Gly Ser Leu Thr Ser
            35              40              45

Gly Val His Thr Phe Pro Ser Val Leu Gln Ser Ser Gly Leu Tyr Ser
```

```
                    50                  55                  60
Leu Ser Ser Met Val Thr Val Pro Ser Ser Arg Trp Pro Ser Glu Thr
 65                  70                  75                  80

Phe Thr Cys Asn Val Ala His Pro Ala Ser Lys Thr Lys Val Asp Lys
                     85                  90                  95

Pro Val Pro Lys Arg Glu Asn Gly Arg Val Pro Arg Pro Pro Asp Cys
                100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
                180                 185                 190

Pro Ile Gly His Gln Asp Trp Leu Lys Gly Lys Gln Phe Thr Cys Lys
                195                 200                 205

Val Asn Asn Lys Ala Leu Pro Ser Pro Ile Glu Arg Thr Ile Ser Lys
210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
                260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
            290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 5
<211> LENGTH: 335
<212> TYPE: PRT
<213> ORGANISM: Canis

<400> SEQUENCE: 5

Ala Ser Thr Thr Ala Pro Ser Val Phe Pro Leu Ala Pro Ser Cys Gly
 1               5                  10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
 50                  55                  60

Leu Ser Ser Met Val Thr Val Pro Ser Ser Arg Trp Pro Ser Glu Thr
 65                  70                  75                  80

Phe Thr Cys Asn Val Ala His Pro Ala Ser Lys Thr Lys Val Asp Lys
                     85                  90                  95

Pro Val Pro Lys Arg Glu Asn Gly Arg Val Pro Arg Pro Pro Asp Cys
```

```
                100             105             110
Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
            130                 135             140

Val Thr Cys Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
            195                 200                 205

Val Asn Asn Lys Ala Leu Pro Ser Pro Ile Glu Arg Thr Ile Ser Lys
            210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
            245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
            275                 280                 285

Asp Gly Ser Tyr Phe Leu Tyr Ser Lys Leu Ser Val Asp Lys Ser Arg
            290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 6
<211> LENGTH: 333
<212> TYPE: PRT
<213> ORGANISM: Canis

<400> SEQUENCE: 6

Ala Ser Thr Thr Ala Pro Ser Val Phe Pro Leu Ala Pro Ser Cys Gly
1               5                   10                  15

Ser Gln Ser Gly Ser Thr Val Ala Leu Ala Cys Leu Val Ser Gly Tyr
            20                  25                  30

Ile Pro Glu Pro Val Thr Val Ser Trp Asn Ser Gly Ser Leu Thr Ser
            35                  40                  45

Gly Val His Thr Phe Pro Ser Ile Leu Gln Ser Ser Gly Leu Tyr Ser
            50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Thr Asn Thr Lys Val Asp Lys
                85                  90                  95

Pro Val Val Lys Glu Cys Glu Cys Lys Cys Asn Cys Asn Asn Cys Pro
            100                 105                 110

Cys Pro Gly Cys Gly Leu Leu Gly Gly Pro Ser Val Phe Ile Phe Pro
            115                 120                 125

Pro Lys Pro Lys Asp Ile Leu Val Thr Ala Arg Thr Pro Thr Val Thr
            130                 135                 140

Cys Val Val Val Asp Leu Asp Pro Glu Asn Pro Glu Val Gln Ile Ser
```

```
                145                 150                 155                 160
Trp Phe Val Asp Gly Lys Gln Met Gln Thr Ala Lys Thr Gln Pro Arg
                    165                 170                 175

Glu Glu Gln Phe Asn Gly Thr Tyr Arg Val Val Ser Val Leu Pro Ile
                180                 185                 190

Gly His Gln Asp Trp Leu Lys Gly Lys Gln Phe Thr Cys Lys Val Asn
                195                 200                 205

Asn Lys Ala Leu Pro Ser Pro Ile Glu Arg Thr Ile Ser Lys Ala Arg
            210                 215                 220

Gly Gln Ala His Gln Pro Ser Val Tyr Val Leu Pro Pro Ser Arg Glu
225                 230                 235                 240

Glu Leu Ser Lys Asn Thr Val Ser Leu Thr Cys Leu Ile Lys Asp Phe
                245                 250                 255

Phe Pro Pro Asp Ile Asp Val Glu Trp Gln Ser Asn Gly Gln Gln Glu
                260                 265                 270

Pro Glu Ser Lys Tyr Arg Thr Thr Pro Pro Gln Leu Asp Glu Asp Gly
                275                 280                 285

Ser Tyr Phe Leu Tyr Ser Lys Leu Ser Val Asp Lys Ser Arg Trp Gln
                290                 295                 300

Arg Gly Asp Thr Phe Ile Cys Ala Val Met His Glu Ser Leu His Asn
305                 310                 315                 320

His Tyr Thr Gln Lys Ser Leu Ser His Ser Pro Gly Lys
                    325                 330

<210> SEQ ID NO 7
<211> LENGTH: 335
<212> TYPE: PRT
<213> ORGANISM: Canis

<400> SEQUENCE: 7

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
                35                  40                  45

Gly Val His Thr Tyr Pro Ser Val Leu Gln Ser Ser Gly Leu Tyr Ser
            50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

Pro Val Pro Lys Arg Glu Asn Gly Arg Val Pro Arg Pro Pro Gly Cys
                100                 105                 110

Pro Lys Cys Pro Ala Pro Glu Met Leu Gly Gly Pro Ser Val Phe Ile
            115                 120                 125

Phe Pro Pro Lys Pro Lys Asp Thr Leu Leu Ile Ala Arg Thr Pro Glu
            130                 135                 140

Val Thr Cys Val Val Val Asp Leu Asp Pro Glu Asp Pro Glu Val Gln
145                 150                 155                 160

Ile Ser Trp Phe Val Asp Ser Lys Gln Val Gln Thr Ala Asn Thr Gln
                165                 170                 175

Pro Arg Glu Glu Gln Ser Asn Gly Thr Tyr Arg Val Val Ser Val Leu
                180                 185                 190

Pro Ile Gly His Gln Asp Trp Leu Ser Gly Lys Gln Phe Lys Cys Lys
```

```
                 195                 200                 205
Val Asn Asn Lys Ala Leu Pro Ser Pro Ile Glu Glu Ile Ile Ser Lys
210                 215                 220

Thr Pro Gly Gln Ala His Gln Pro Asn Val Tyr Val Leu Pro Pro Ser
225                 230                 235                 240

Arg Asp Glu Met Ser Lys Asn Thr Val Thr Leu Thr Cys Leu Val Lys
                245                 250                 255

Asp Phe Phe Pro Pro Glu Ile Asp Val Glu Trp Gln Ser Asn Gly Gln
                260                 265                 270

Gln Glu Pro Glu Ser Lys Tyr Arg Met Thr Pro Pro Gln Leu Asp Glu
                275                 280                 285

Asp Gly Ser Tyr Phe Leu Tyr Ser Lys Leu Ser Val Asp Lys Ser Arg
                290                 295                 300

Trp Gln Arg Gly Asp Thr Phe Ile Cys Ala Val Met His Glu Ala Leu
305                 310                 315                 320

His Asn His Tyr Thr Gln Lys Ser Leu Ser His Ser Pro Gly Lys
                325                 330                 335

<210> SEQ ID NO 8
<211> LENGTH: 109
<212> TYPE: PRT
<213> ORGANISM: Canis

<400> SEQUENCE: 8

Asn Asp Ala Gln Pro Ala Val Tyr Leu Phe Gln Pro Ser Pro Asp Gln
1               5                   10                  15

Leu His Thr Gly Ser Ala Ser Val Val Cys Leu Leu Asn Ser Phe Tyr
                20                  25                  30

Pro Lys Asp Ile Asn Val Lys Trp Lys Val Asp Gly Val Ile Gln Asp
            35                  40                  45

Thr Gly Ile Gln Glu Ser Val Thr Glu Gln Asp Lys Asp Ser Thr Tyr
        50                  55                  60

Ser Leu Ser Ser Thr Leu Thr Met Ser Ser Thr Glu Tyr Leu Ser His
65                  70                  75                  80

Glu Leu Tyr Ser Cys Glu Ile Thr His Lys Ser Leu Pro Ser Thr Leu
                85                  90                  95

Ile Lys Ser Phe Gln Arg Ser Glu Cys Gln Arg Val Asp
            100                 105

<210> SEQ ID NO 9
<211> LENGTH: 106
<212> TYPE: PRT
<213> ORGANISM: Canis

<400> SEQUENCE: 9

Gly Gln Pro Lys Ala Ser Pro Ser Val Thr Leu Phe Pro Pro Ser Ser
1               5                   10                  15

Glu Glu Leu Gly Ala Asn Lys Ala Thr Leu Val Cys Leu Ile Ser Asp
                20                  25                  30

Phe Tyr Pro Ser Gly Val Thr Val Ala Trp Lys Ala Asp Gly Ser Pro
            35                  40                  45

Ile Thr Gln Gly Val Glu Thr Thr Lys Pro Ser Lys Gln Ser Asn Asn
        50                  55                  60

Lys Tyr Ala Ala Ser Ser Tyr Leu Ser Leu Thr Pro Asp Lys Trp Lys
65                  70                  75                  80

Ser His Ser Ser Phe Ser Cys Leu Val Thr His Glu Gly Ser Thr Val
                85                  90                  95
```

```
Glu Lys Lys Val Ala Pro Ala Glu Cys Ser
            100                 105

<210> SEQ ID NO 10
<211> LENGTH: 335
<212> TYPE: PRT
<213> ORGANISM: Felis

<400> SEQUENCE: 10

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asp Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 11
<211> LENGTH: 335
<212> TYPE: PRT
<213> ORGANISM: Felis
```

```
<400> SEQUENCE: 11

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val Arg Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 12
<211> LENGTH: 335
<212> TYPE: PRT
<213> ORGANISM: Felis

<400> SEQUENCE: 12

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ser Val Leu Gln Ala Ser Gly Leu Tyr Ser
 50                  55                  60

Leu Ser Ser Met Val Thr Val Pro Ser Ser Arg Trp Leu Ser Asp Thr
 65                  70                  75                  80

Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
                100                 105                 110

Pro Lys Cys Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 13
<211> LENGTH: 335
<212> TYPE: PRT
<213> ORGANISM: Felis

<400> SEQUENCE: 13

Ala Ser Thr Thr Ala Pro Ser Val Phe Pro Leu Ala Pro Ser Cys Gly
 1               5                  10                  15

Thr Thr Ser Gly Ala Thr Val Ala Leu Ala Cys Leu Val Leu Gly Tyr
             20                  25                  30

Phe Pro Glu Pro Val Thr Val Ser Trp Asn Ser Gly Ala Leu Thr Ser
            35                  40                  45

Gly Val His Thr Phe Pro Ser Val Leu Gln Ala Ser Gly Leu Tyr Ser
 50                  55                  60

Leu Ser Ser Met Val Thr Val Pro Ser Ser Arg Trp Leu Ser Asp Thr
 65                  70                  75                  80
```

```
Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Pro
            180                 185                 190

Pro Ile Leu His Gln Asp Trp Leu Thr Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 14
<211> LENGTH: 334
<212> TYPE: PRT
<213> ORGANISM: Felis

<400> SEQUENCE: 14

Ser Thr Thr Ala Pro Ser Val Phe Pro Leu Ala Pro Ser Cys Gly Thr
1               5                   10                  15

Thr Ser Gly Ala Thr Val Ala Leu Ala Cys Leu Val Leu Gly Tyr Phe
            20                  25                  30

Pro Glu Pro Val Thr Val Ser Trp Asn Ser Gly Ala Leu Thr Ser Gly
        35                  40                  45

Val His Thr Phe Pro Ser Val Leu Gln Ala Ser Gly Leu Tyr Ser Leu
    50                  55                  60

Ser Ser Met Val Thr Val Pro Ser Ser Arg Trp Leu Ser Asp Thr Phe
65                  70                  75                  80

Thr Cys Asn Val Ala His Pro Pro Ser Asn Thr Lys Val Asp Lys Ala
                85                  90                  95

Val Arg Lys Thr Asp His Pro Pro Gly Pro Lys Pro Cys Asp Cys Pro
            100                 105                 110

Lys Cys Pro Pro Pro Glu Met Leu Gly Gly Pro Ser Ile Phe Ile Phe
        115                 120                 125
```

```
Pro Pro Lys Pro Lys Asp Thr Leu Ser Ile Ser Arg Thr Pro Glu Val
            130                 135                 140

Thr Cys Leu Val Val Asp Leu Gly Pro Asp Asp Ser Asp Val Gln Ile
145                 150                 155                 160

Thr Trp Phe Val Asp Asn Thr Gln Val Tyr Thr Ala Lys Thr Ser Pro
                    165                 170                 175

Arg Glu Glu Gln Phe Asn Ser Thr Tyr Arg Val Val Ser Val Leu Pro
                180                 185                 190

Ile Leu His Gln Asp Trp Leu Lys Gly Lys Glu Phe Lys Cys Lys Val
            195                 200                 205

Asn Ser Lys Ser Leu Pro Ser Pro Ile Glu Arg Thr Ile Ser Lys Asp
210                 215                 220

Lys Gly Gln Pro His Glu Pro Gln Val Tyr Val Leu Pro Pro Ala Gln
225                 230                 235                 240

Glu Glu Leu Ser Arg Asn Lys Val Ser Val Thr Cys Leu Ile Glu Gly
                245                 250                 255

Phe Tyr Pro Ser Asp Ile Ala Val Glu Trp Glu Ile Thr Gly Gln Pro
                260                 265                 270

Glu Pro Glu Asn Asn Tyr Arg Thr Thr Pro Pro Gln Leu Asp Ser Asp
            275                 280                 285

Gly Thr Tyr Phe Leu Tyr Ser Arg Leu Ser Val Asp Arg Ser Arg Trp
        290                 295                 300

Gln Arg Gly Asn Thr Tyr Thr Cys Ser Val Ser His Glu Ala Leu His
305                 310                 315                 320

Ser His His Thr Gln Lys Ser Leu Thr His Ser Pro Gly Lys
                325                 330

<210> SEQ ID NO 15
<211> LENGTH: 335
<212> TYPE: PRT
<213> ORGANISM: Felis

<400> SEQUENCE: 15

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175
```

```
Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Leu Tyr Ser Arg Leu Ser Val Asp Arg Ser Arg
290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
                325                 330                 335

<210> SEQ ID NO 16
<211> LENGTH: 335
<212> TYPE: PRT
<213> ORGANISM: Felis

<400> SEQUENCE: 16

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ser Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
210                 215                 220
```

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Leu Tyr Ser Arg Leu Ser Val Asp Arg Ser Arg
    290                 295                 300

Trp Gln Arg Gly Asn Thr Tyr Thr Cys Pro Val Ser His Glu Ala Leu
305                 310                 315                 320

His Ser His His Thr Gln Lys Ser Leu Thr His Ser Pro Gly Lys
                325                 330                 335

<210> SEQ ID NO 17
<211> LENGTH: 335
<212> TYPE: PRT
<213> ORGANISM: Felis

<400> SEQUENCE: 17

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Pro Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Gln
            260                 265                 270

Pro Glu Pro Glu Asn Asn Tyr Arg Thr Thr Pro Gln Leu Asp Ser
            275                 280                 285

Asp Gly Thr Tyr Phe Leu Tyr Ser Arg Leu Ser Val Asp Arg Ser Arg
        290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
            325                 330                 335

<210> SEQ ID NO 18
<211> LENGTH: 335
<212> TYPE: PRT
<213> ORGANISM: Canis

<400> SEQUENCE: 18

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly Lys
            325                 330                 335

<210> SEQ ID NO 19
<211> LENGTH: 334
<212> TYPE: PRT
<213> ORGANISM: Felis

<400> SEQUENCE: 19

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Arg Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr His Ser Pro Gly
                325                 330

<210> SEQ ID NO 20
<211> LENGTH: 336
<212> TYPE: PRT
<213> ORGANISM: Felis

-continued

<400> SEQUENCE: 20

```
Ala Ser Thr Thr Ala Pro Ser Val Phe Pro Leu Ala Pro Ser Cys Gly
 1               5                   10                  15

Thr Thr Ser Gly Ala Thr Val Ala Leu Ala Cys Leu Val Leu Gly Tyr
             20                  25                  30

Phe Pro Glu Pro Val Thr Val Ser Trp Asn Ser Gly Ala Leu Thr Ser
         35                  40                  45

Gly Val His Thr Phe Pro Ser Val Leu Gln Ala Ser Gly Leu Tyr Ser
     50                  55                  60

Leu Ser Ser Met Val Thr Val Pro Ser Ser Arg Trp Leu Ser Asp Thr
 65                  70                  75                  80

Phe Thr Cys Asn Val Ala His Pro Pro Ser Asn Thr Lys Val Asp Lys
                 85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
210                 215                 220

Asp Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Glu
                245                 250                 255

Gly Phe Tyr Pro Ser Asp Ile Ala Val Glu Trp Glu Ile Thr Gly Thr
            260                 265                 270

Ala Gly Ala Arg Glu Gln Leu Pro Gly Arg Pro Arg Pro Ser Trp Asn
        275                 280                 285

Ser Asp Gly Thr Tyr Phe Leu Tyr Ser Arg Leu Ser Val Asp Arg Ser
290                 295                 300

Arg Trp Gln Arg Gly Asn Thr Tyr Thr Cys Ser Val Ser His Glu Ala
305                 310                 315                 320

Leu His Ser His His Thr Gln Lys Ser Leu Thr His Ser Pro Gly Lys
                325                 330                 335
```

<210> SEQ ID NO 21
<211> LENGTH: 110
<212> TYPE: PRT
<213> ORGANISM: Felis

<400> SEQUENCE: 21

```
Arg Ser Asp Ala Gln Pro Ser Val Phe Leu Phe Gln Pro Ser Leu Asp
 1               5                   10                  15

Glu Leu His Thr Gly Ser Ala Ser Ile Val Cys Ile Leu Asn Asp Phe
             20                  25                  30

Tyr Pro Lys Glu Val Asn Val Lys Trp Lys Val Asp Gly Val Val Gln
```

```
                   35                  40                  45
Asn Lys Gly Ile Gln Glu Ser Thr Thr Glu Gln Asn Ser Lys Asp Ser
     50                  55                  60

Thr Tyr Ser Leu Ser Ser Thr Leu Thr Met Ser Ser Thr Glu Tyr Gln
65                  70                  75                  80

Ser His Glu Lys Phe Ser Cys Glu Val Thr His Lys Ser Leu Ala Ser
                 85                  90                  95

Thr Leu Val Lys Ser Phe Asn Arg Ser Glu Cys Gln Arg Glu
                100                 105                 110

<210> SEQ ID NO 22
<211> LENGTH: 24
<212> TYPE: DNA
<213> ORGANISM: Felis

<400> SEQUENCE: 22
gctagcacca cggccccatc ggtg                                          24

<210> SEQ ID NO 23
<211> LENGTH: 26
<212> TYPE: DNA
<213> ORGANISM: Felis

<400> SEQUENCE: 23
ggatcctcat ttacccggag aatggg                                        26

<210> SEQ ID NO 24
<211> LENGTH: 23
<212> TYPE: DNA
<213> ORGANISM: Felis

<400> SEQUENCE: 24
ctcgagatca aacggagtga tgc                                           23

<210> SEQ ID NO 25
<211> LENGTH: 24
<212> TYPE: DNA
<213> ORGANISM: Felis

<400> SEQUENCE: 25
ggatccctac tctctctgac actc                                          24
```

ANTIBODY CONSTANT DOMAIN REGIONS AND USES THEREOF

CROSS REFERENCE TO RELATED APPLICATIONS

This application claims the benefit of U.S. Provisional Application No. 61/163,194 filed on Mar. 25, 2009, the contents of which is incorporated herein by reference.

FIELD OF THE INVENTION

The field relates to treatment of diseases, e.g., in companion animals, involving a recombinant polypeptide composition including an antibody constant domain region and to methods for production of such recombinant polypeptides.

BACKGROUND OF THE INVENTION

The use of immunoglobulins as therapeutic treatment for a variety of diseases and disorders is rapidly increasing because they have shown to be safe and efficacious therapeutic agents. Approved therapeutic monoclonal antibodies for human use include Trastuzumab (antigen: 180 kD, HER2/neu), Edrecolomab (antigen: 40-50 kD, Ep-CAM), Anti-human milk fat globules (HMFG1) (antigen>200 kD, HMW Mucin), Cetuximab (antigens: 150 kD and 170 kD, EGF receptor), Alemtuzumab (antigen: 21-28 kD, CD52), and Rituximab (antigen: 35 kD, CD20). The extracellular domains of membrane-bound receptors in the immunoglobulin superfamily may be fused to antibody constant domains, or fragments thereof, to form soluble receptors having antibody-like structure and function. Approved therapeutic proteins containing constant domains derived from antibodies for human use include etanercept, a fusion of the TNF receptor and an Fc domain from human IgG1. Additional therapeutic proteins are in various phases of clinical development for humans for a variety of diseases with the majority targeting various forms of cancer and inflammatory-related diseases.

Antibodies target an antigen through its binding of a specific epitope on an antigen by the interaction with the variable region of the antibody molecule. At the same time, the constant region of the antibody may additionally recruit other cells or molecules for example to destroy the cell or protein to which the antibody is bound or trigger further immune reactions. Certain regions of the immunoglobulin constant domain may elicit antibody-mediated cytotoxicity (ADCC), complement-mediated cytotoxicity (CDC), phagocytosis, immediate hypersensitivity, regulation of the Ig synthesis, and antigen presenting cells. The ability of the immunoglobulin constant domain regions to bind to certain receptors on certain types of cells is a feature that can be exploited to alter the effects of a polypeptide including these constant domain regions and/or fragment thereof. In some cases, for example, it might be desirable to lyse the cell to which the antibody binds; in other cases, not. This function can be controlled by manipulation of the constant domain.

Whereas the structural features and biological functions of the constant domain regions have been intensively studied in several mammalian species such as humans and mice, they have been less studied in companion animals such as canine, feline, and equine mammals. A recombinant polypeptide containing a modified Ig constant domain region or fragment thereof may enhance the therapeutic efficacy of a recombinant monoclonal antibody or Ig-fusion protein for companion animals such as dogs, cats and horses.

SUMMARY OF THE INVENTION

The invention provides recombinant proteins (e.g., a recombinant antibody or soluble receptor) having (i) a binding domain capable of specific binding to an epitope (for example an antibody variable domains, a receptor, a growth factor, a cytokine, or a fragment of any of the foregoing which is capable of specifically binding the desired epitope) and (ii) an effector domain comprising a constant domain region which is derived from immunoglobulin of companion mammals, e.g. dogs, cats, or horses, having engineered substitutions at one or more positions.

In one embodiment, a constant domain region of the invention is one that has an altered interaction with one or more FcRs or other ligands, and optionally enhanced effector function, relative to the parent constant domain region.

In another embodiment, a constant domain region does not interact with one or more FcRs or other constant domain ligands, and the introduction of one or more substituted positions and/or substitutions of the invention to the parent constant domain region sequence yields an altered constant domain region of the invention that has enhanced interaction with one or more FcRs or constant domain ligands and optionally has enhanced effector functions, relative to the parent Fc region.

In one embodiment, a parent constant domain region has effector function, e.g., elicits ADCC, and the introduction of one or more substituted positions and/or substitutions of the invention, yields an altered constant domain region with enhanced effector function relative to parent constant domain region.

Exemplary effector functions include ADCC, complement-dependent cytotoxicity (CDC), antibody-dependent cell mediated phagocytosis (ADCP), a cell-mediated reaction where nonspecific cytotoxic cells that express FcγRs recognize bound antibody on a target cell and subsequently cause phagocytosis of the target cell down regulation of cell surface receptors and the like. Such effector functions generally require the constant domain region to be combined with a binding domain (e.g., an antibody variable domain). Methods to detect FcR binding and effector function are known in the art.

In one embodiment, a recombinant Ig protein with a constant domain region or fragment thereof isolated and/or engineered for increased binding to one or more receptors present on particular cells of the patient may improve the interaction with FcR-related functions and thereby be more effective.

In yet another embodiment, a recombinant Ig protein with a constant domain region or fragment thereof isolated and/or engineered for decreased binding to one or more receptors present on particular cells of the patient may improve its functions and thereby be more effective.

Thus, in one embodiment, a recombinant Ig protein which include a constant domain region, besides specifically binding a target molecule or antigen may also have other activities such as eliciting immune effector mechanisms, e.g., enhanced immune effector mechanism such as enhancement of cytotoxic effector functions such as ADCC, antibody dependent cellular phagocytosis (ADCP), complement dependent cytotoxicity (CDC), and alteration of in vivo half-life relative to a corresponding wild-type protein or parent polypeptide without a constant domain region of the invention or with an unaltered constant domain region of the invention.

Accordingly, in certain embodiments, a recombinant polypeptide includes a constant domain region or fragment thereof of an isolated constant domain region or an isolated constant domain region with engineered substitutions relative to the constant domain region at one or more positions with any possible combinations of those positions.

DETAILED DESCRIPTION OF THE INVENTION

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a subject polypeptide" includes a plurality of such polypeptides and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, tissue culture and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). See e.g., Harlow and Lane. Antibodies: A Laboratory Manual (Cold Spring Harbor Laboratory Press, Cold Spring Harbor, N.Y. (1988)).

Methods for the isolation and the engineering of a constant domain regions and/or fragments thereof to create a recombinant polypeptide suitable for the treatment of animals and as diagnostic agents are described herein. The recombinant polypeptide of the composition includes the constant domain region or a fragment thereof fused to a protein or a fragment thereof that is capable of specific binding to an epitope. The protein or fragment can be the variable domains or fragment thereof from an antibody, can be a receptor or a fragment thereof, can be a growth factor or a fragment thereof, a peptide or a fragment thereof and the like.

Recombinant polypeptides disclosed herein present several advantages, such as (i) increased potency mediated by an efficient recruitment of the immune system and/or pertinent cells in the targeted species; (ii) increased potency by an alteration of the interaction of the constant domain regions with the immune system and/or relevant cells in the targeted species; (iii) increased half-life; (iv) reduced immunogenicity response upon repeated administration.

Generation of polypeptides and/or fragments thereof containing the constant domain regions of the invention with the desired properties and their use in production are also disclosed. The recombinant polypeptide of the present invention comprises a native or engineered full-length protein or a fragment thereof from protein such as the variable domain of an antibody, or a receptor, or a peptide fused to the constant domain regions of the invention. Thus, the polypeptide of the invention retains the specificities and high affinities with the desired effector functions in the target species.

"Native antibodies" are usually glycoproteins of about 150,000 daltons, composed of two identical light chains and two identical heavy chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain.

The "light chains" of antibodies from any vertebrate species can be assigned to one of two clearly distinct types, called kappa and lambda.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, or IgG-A, IgG-B, IgG-C, IgG-D. The heavy-chain constant domains corresponding to the different classes of immunoglobulins are called alpha, delta, epsilon, gamma, and mu, respectively.

The term "variable domain" usually refers to the fact that certain portions of the variable domains differ in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4). The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to readily crystallize. Pepsin treatment yields a binding cross-linking antigen.

"Fv" is the minimum antibody fragment which contains a complete antigen-recognition and -binding site. This region consists of a dimer of one heavy chain and one light chain variable domain.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" refers to the C-terminal region of an immunoglobulin heavy chain. Although the boundaries of the Fc region might vary, the Fc region generally comprises two constant domains, CH2 and CH3.

The term "constant domain" refers to a region of an immunoglobulin light chain or heavy chain that is distinct from the variable domain. The constant domain of the heavy chain generally comprises several constant domains (CH1, Hinge, CH2, and CH3).

The term "antibody" herein is used in the broadest sense and specifically covers monoclonal antibodies (including full length monoclonal antibodies), polyclonal antibodies, multispecific antibodies (e.g., bispecific antibodies), and antibody fragments exhibiting the desired biological activity.

"Antibody fragments" or "antigen-binding moiety" comprise a portion of a full length antibody, generally the antigen binding or variable domain thereof. Examples of antibody fragments include Fab, Fab', F(ab')$_2$, and Fv fragments; diabodies; linear antibodies; single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific. For example, the monoclonal antibodies to be used in accordance with the present invention may be made by the hybridoma method first described by Kohler et al., Nature 256:495 (1975), or may be made by recombinant DNA methods. The "monoclonal antibodies" may also be isolated from phage antibody libraries.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, exhibiting the desired biological activity (U.S. Pat. No. 4,816,567; and Morrison et al., Proc. Natl. Acad. Sci. USA 81:6851-6855 (1984)).

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is short to allow pairing between the two domains on the same chain, the domains are forced to pair with the complementary domains of another chain and create two antigen-binding sites.

The term "immunoconjugates" refers antibody or fragment thereof conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different molecules, e.g., different antigens, or different epitopes on the same molecule).

The term "specificity" refers to the ability to specifically bind (e.g., immunoreact with) a given target. A polypeptide may be monospecific and contain one or more binding sites which specifically bind a target or a polypeptide may be multispecific (e.g., bispecific or trispecific) and contain two or more binding sites which specifically bind the same or different targets Monoclonal antibodies are most frequently generated in mice by administration of the "antigen" and subsequent isolation of B-cells that make antibodies. The B-cells are then immortalized by fusion to another, stable cell type of the same species of the B cell to create a "hybridoma". An individual B-cell makes one specific antibody that is defined by its primary amino acid sequence and its underlying gene sequence.

The terms "fragment" and "region" refer to portions of a polypeptide or nucleic acid molecule that contains at least 10%, 20%, 30%, 40%, 50%, 60%, 70%, 80%, 90%, 95%, or more of the entire length of the reference nucleic acid molecule or polypeptide.

The terms "polynucleotide," "nucleic acid," and "nucleic acid molecule," are used interchangeably herein to refer to polymeric forms of nucleotides of any length. The polynucleotides can contain deoxyribonucleotides, ribonucleotides, and/or their analogs. Polynucleotides can have any three-dimensional structure, and can perform any function, known or unknown. The term polynucleotide includes single-stranded, double-stranded, and triple helical molecules, and encompasses nucleic acids containing nucleotide analogs or modified backbone residues or linkages, which can be synthetic, naturally occurring, or non-naturally occurring, and which have similar binding properties as the reference nucleic acid.

"Oligonucleotide" refers generally to polynucleotides that are between 5 and about 100 nucleotides of single- or double-stranded DNA. For the purposes of this disclosure, the lower limit of the size of an oligonucleotide is two, and there is no upper limit to the length of an oligonucleotide. Oligonucleotides are also known as "oligomers" or "oligos" and can be prepared by any method known in the art including isolation from naturally-occurring polynucleotides, enzymatic synthesis and chemical synthesis.

The terms "polypeptide," "peptide" and "protein" are used interchangeably herein to refer to a polymer of amino acid residues of any length. Polypeptides can have any three-dimensional structure, and can perform any function, known or unknown. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ carboxyglutamate, and O-phosphoserine. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "conservatively modified variants" or "conservative variants" applies to both amino acid and nucleic acid sequences. With respect to particular nucleic acid sequences, conservatively modified variants refers to those nucleic acids which encode identical or substantially identical amino acid sequences; or for nucleic acids that do not encode an amino acid sequence, to nucleic acids that are substantially identical. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the alternate alanine codons without altering the encoded polypeptide. Such nucleic acid variations are "silent variations," which are one type of conservatively modified variants. Nucleic acid sequences encoding polypeptides described herein also encompass every possible silent variation of the nucleic acid. The skilled artisan will recognize that each amino acid codon in a nucleic acid (except AUG, which is ordinarily the only codon for methionine, and TGG, which is ordinarily the only codon for tryptophan) can be varied at one or more positions to code for the same amino acid. Accordingly, each silent variation of a nucleic acid that encodes a polypeptide is implicit in each described sequence with respect to the expression product.

"Complementarity" as applied to nucleic acids, refers to the ability of the nucleic acid to form hydrogen bond(s) with another polynucleotide sequence by either traditional Watson-Crick or other non-traditional types of base pairing. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, RNA interference, antisense or triple helix inhibition. Determination of binding free energies for nucleic acid molecules is well known in the art. "Percent complementarity" refers to the percentage of contiguous residues in a nucleic acid molecule that can form hydrogen bonds (e.g., Watson-Crick base pairing) with another nucleic acid molecule. "Perfectly complementary" or "100% complementarity" means that all the contiguous nucleotides of a nucleic acid molecule will hydrogen bond with the same number of contiguous residues in a second nucleic acid molecule. "Substantial complementarity" and "substantially complementary" as used herein indicate that two nucleic acids are at least 90% complementary, typically at least 95% complementary, often at least 98% complementary, and most frequently at least 99% complementary over a region of more than about 15 nucleotides and more often more than about 19 nucleotides.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like). In certain embodiments, a homolog can be found in a non-native position in the genome, e.g. as the result of translocation.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

The term "homolog" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence.

"Similar" sequences are those which, when aligned, share identical and similar amino acid residues, where similar residues are conservative substitutions for corresponding amino acid residues in an aligned reference sequence. In this regard, conservative residues in a sequence is a residue that is physically or functionally similar to the corresponding reference residue, e.g., that has a similar size, shape, electric charge, chemical properties, including the ability to form covalent or hydrogen bonds, or the like. The "percentage similarity" between two sequences is a function of the number of positions that contain matching residues or conservative residues shared by the two sequences divided by the number of positions compared.times.100.

"Amino acid consensus sequence" as used herein refers to a hypothetical amino acid sequence that can be generated using a matrix of at least two, and preferably more, aligned amino acid sequences, and allowing for gaps in the alignment, such that it is possible to determine the most frequent amino acid residue at each position. The consensus sequence is that sequence which comprises the amino acids which are most frequently represented at each position. In the event that two or more amino acids are equally represented at a single position, the consensus sequence includes both or all of those amino acids. In some cases, amino acid consensus sequences correspond to a sequence or sub-sequence found in nature. In other cases, amino acid consensus sequences are not found in nature, but represent only theoretical sequences.

The amino acid sequence of a protein can be analyzed at various levels. For example, conservation or variability can be exhibited at the single residue level, multiple residue level, multiple residues with gaps etc. Residues can exhibit conservation of the identical residue or can be conserved at the class level. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). Other classes are known to one of skill in the art and may be defined using structural determinations or other data to assess substitutability.

Regarding amino acid sequences, one of skill in the art will recognize that individual substitutions, deletions or insertions to a nucleic acid, peptide, polypeptide, or protein sequence which alters, inserts or deletes a single amino acid or a small percentage of amino acids in the encoded sequence is a "conservatively modified variant" where the alteration results in the substitution of an amino acid with a chemically similar amino acid. Conservative substitution tables detailing functionally similar amino acids are well known in the art. Such conservatively modified variants are in addition to and do not exclude functionally equivalent polymorphic variants, homologs, and alleles of the invention.

As used herein, when one amino acid sequence (e.g., a first VH or VL sequence) is aligned with one or more additional amino acid sequences (e.g., one or more VH or VL sequences in a database), an amino acid position in one sequence (e.g., the first VH or VL sequence) can be compared to a "corresponding position" in the one or more additional amino acid sequences. As used herein, the "corresponding position" represents the equivalent position in the sequence(s) being compared when the sequences are optimally aligned, i.e., when the sequences are aligned to achieve the highest percent identity or percent similarity.

As used herein, the term "antibody database" refers to a collection of two or more antibody amino acid sequences (a "plurality" or "multiplicity" of sequences), and typically refers to a collection of tens, hundreds or even thousands of antibody amino acid sequences. An antibody database can store amino acid sequences of, for example, a collection of antibody VH regions, antibody VL regions or both, or can store a collection of framework sequences. In one embodiment, the antibody database is a database comprising or consisting of germline antibody sequences. In another embodiment, the antibody database is a database comprising or consisting of mature antibody sequences (e.g., a Kabat database of mature antibody sequences). In another embodiment, the antibody database comprises or consists of sequences selected for one or more properties. In another embodiment, the antibody database comprises or consists of consensus sequences. In another embodiment, the antibody database comprises or consists of similar sequences. In yet another embodiment, the antibody database comprises or consists of sequences from major antibody clans (Das et al., *Immunogenetics*, 60:47-55 (2008); Das et al., *Proc. Natl. Ac. Sci. USA*. 105:16647-16652 (2008)).

As used herein the term "derived from" a designated protein refers to the origin of the polypeptide. In one embodiment, the polypeptide or amino acid sequence which is derived from a particular starting polypeptide is a constant domain region sequence or sequence related thereto. In one embodiment, the amino acid sequence which is derived from a particular starting polypeptide is not contiguous. In one embodiment, the polypeptide or amino acid sequence that is derived from a particular starting polypeptide or amino acid sequence has an amino acid sequence that is essentially identical to that of the starting sequence or a portion thereof, wherein the portion consists of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence.

A polypeptide variant or a recombinant antibody variant or a recombinant antibody molecule or a variant with "altered" effector function is one which has either enhanced or diminished activity compared to a reference polypeptide. A reference polypeptide can be a non-recombinant polypeptide comprising a constant domain region, an isolated polypeptide comprising a native constant domain, a recombinant polypeptide comprising a native constant domain, or a recombinant polypeptide comprising an engineered constant domain region.

The polypeptide variant which mediates antibody-dependent cell-mediated cytotoxicity (ADCC) in the presence of effector cells more effectively than a reference polypeptide is one which in vitro or in vivo is substantially more effective at mediating ADCC, when the amounts of polypeptide variant and reference polypeptide used in the assay are essentially the same. Generally, such variants will be identified using the in vitro ADCC assay as herein disclosed, but other assays or methods for determining ADCC activity are contemplated.

The polypeptide variant which mediates complement-dependent cytotoxicity (CDC) in the presence of complement more effectively than a reference polypeptide is one which in vitro or in vivo is substantially more effective at mediating CDC, when the amounts of polypeptide variant and reference polypeptide used in the assay are essentially the same. Generally, such variants will be identified using the in vitro CDC assay as herein disclosed, but other assays or methods for determining CDC activity are contemplated.

As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques).

A polypeptide variant or a recombinant antibody variant or a recombinant antibody molecule or a variant comprises an amino acid sequence which differs from that of a reference sequence by virtue of at least one amino acid addition, deletion, or substitution. Variants include sequences of native antibodies as well as naturally occurring variants, and recombinant polypeptides. The polypeptide variant (s) may be subjected to further modification, oftentimes depending on the intended use of the polypeptide.

As used herein, the term "property" is a property of a polypeptide which is desirable and/or advantageous to one of skill in the art, e.g., in order to improve the manufacturing properties or therapeutic efficacy of the polypeptide. In one embodiment, the functional property is improved stability. In another embodiment, the functional property is improved solubility. In yet another embodiment, the functional property is non-aggregation. In still another embodiment, the functional property is an improvement in expression. In certain embodiments, the functional property is an improvement in antigen binding affinity.

As used herein the term "protein stability" refers to an art-recognized measure of the maintenance of one or more physical properties of a protein in response to an environmental condition (e.g. an elevated or lowered temperature). In one embodiment, the physical property is the maintenance of the covalent structure of the protein (e.g. the absence of proteolytic cleavage, unwanted oxidation or deamidation). In another embodiment, the physical property is the presence of the protein in a properly folded state (e.g. the absence of soluble or insoluble aggregates or precipitates). In one embodiment, stability of a protein is measured by assaying a biophysical property of the protein, for example thermal stability, pH unfolding profile, stable removal of glycosylation, solubility, biochemical function (e.g., ability to bind to a protein (e.g., a ligand, a receptor, an antigen, etc.) or chemical moiety, etc.), and/or combinations thereof. In another embodiment, biochemical function is demonstrated by the binding affinity of an interaction. In one embodiment, a measure of protein stability is thermal stability, i.e., resistance to thermal challenge. Stability can be measured using methods known in the art and/or described herein.

The term "TM", also referred to as the "transition temperature", is the temperature at which 50% of a macromolecule, e.g., binding molecule, becomes denatured, and is considered to be the standard parameter for describing the thermal stability of a protein.

As used herein the term "Ig fold" includes a protein domain found in proteins belonging to the immunoglobulin superfamily of proteins. As is well known in the art, the Ig fold is a distinguishing feature of the immunoglobulin superfamily.

The source of the constant domain regions of the present invention may be from any antibody class (isotype), any organism, including but not limited to mammals, preferably dogs, cats, and horses or any source, e.g., a previously engineered antibody, e.g., a chimeric antibody or a recombinant antibody including variants modified in vitro, or selected in vitro or in vivo. Alternatively, the source of a constant domain region is from a naturally occurring antibody, including IgG, IgD, IgM, IgE, IgA. A constant domain is preferably one that interacts with one or more FcRs or other ligands, e.g., Fc ligands include but are not limited to FcγRs, FcαRs, FcERs, FcµRs, FcδRs, FcRn, C1q, C3, lectin, mannose receptor, staphylococcal protein A, and streptococcal protein G.

FcRs are defined by their specificity for immunoglobulin isotypes. For example, FcRs for IgG antibodies are referred to as FcγR, those for IgE as FceR and those for IgA as FcαR. Another type of FcR is the neonatal FcR (FcRn).

The Fc portion of an antibody is composed of the hinge and constant domains (CH2 and CH3), performs two basic functions: communication with the immune system and regulation of half-life of (Jefferis, Antibody therapeutics: isotype and glycoform selection, Exp Opin Biol Ther 7 (2007), pp. 1401-1413; Salfeld, Isotype selection in antibody engineering, Nat Biotechnol 25 (2007), pp. 1369-1372; Presta, Molecular engineering and design of therapeutic antibodies Current Opinion in Immunology (2008) 20, 460-470). First, it communicates with the immune system once the antibody has bound its target by via effector functions: antibody-dependent cellular cytotoxicity (ADCC), antibody-dependent cellular phagocytosis (ADCP), and complement-dependent cytotoxicity (CDC). The first two are mediated by interaction of the Fc with specific receptors, FcγR, expressed on a variety of immune system cells such as natural killer cells, monocytes, neutrophils, and macrophages. By contrast, CDC is mediated through interaction of the Fc with a series of blood proteins that constitute the complement system, including C1q.

FcRs are separated into four main classes differing by their ligand preferences, binding affinity, and signal properties: FcgRI (the high affinity receptor for IgG), FceRI (high affinity receptor for IgE), and low affinity receptors for IgG FcgRII and FcgRIII (Ravetch and Kinet 1(991) Fc receptors. Annu Rev Immunol 9:457-492; Daeron (1997) Fc receptor biology. Annu Rev Immunol 5:203-234; Maltais Lovering, Taranin, Colonna, Ravetch, Dalla-Favera, Burrows, Cooper, Davis (2006) New nomenclature for Fc receptor-like molecules. Nat Immunol 7:431-432). The Ig-like domains of the FcR extracellular regions may be separated into three structural subtypes: D1, D2, and D3. FcgRI has all the three subtypes, whereas extracellular regions of the other FcRs are composed of D1 and D2. Studies of the human and mouse FcRs has demonstrated that the family evolved in a species-specific manner. In the human genome, there is a single functional gene for FcgRI and FceRI, three for FcgRII (FcgRIIa, FcgRIIb, and FcgRIIc), and two for FcgRIII (FcgRIIIa and FcgRIIIb). In addition, human has two putative FcgRI pseudogenes. FcgRIIb contains immunoreceptor tyrosine based inhibitory motif (ITIM) in its cytoplasmic (IC) region and functions as an inhibitory receptor; the other FcRs promote leukocyte activation programs. FcgRI, FceRI, and FcgRIIIa are expressed on the cell surface in complex with immunoreceptor tyrosine-based activating motif (ITAM). Four genes encoding Fc receptors have been identified in mouse: one for each FcgRI, FcgRII, FcgRIII, and FceRI class.

All the three subsets of the FcR-family are maintained throughout the mammalian evolution and have been identified in the dog genome. However, their comparison has shown that the sequences were subjected to continuous reorganization and support the concept that each repertoire contributes to the species-specific immuno-regulation (Davis, Dennis, Odom, Gibson, Kimberly, Burrows, and Cooper M D (2002) Fc receptor homologs: newest members of a remarkably diverse Fc receptor gene family. Immunol Rev 190:123-136; Davis, Ehrhardt, Leu, Hirand, Cooper (2005) An extended family of Fc receptor relatives. Eur J Immunol 35:674-680; Fayngerts, Alexander, Najakshin, and Taranin (2007) Species-specific evolution of the FcR family in endothermic vertebrates. Immunogenetics 59:493-506).

Examples of participation of the canine immune cells in various immune reactions, such as phagocytosis and antibody-dependent cellular cytotoxicity have been reported (Helfand, Hank, Gan and Sondel. Lysis of Human Tumor Cell Lines by Canine Complement plus Monoclonal Antiganglioside Antibodies or Natural Canine Xenoantibodies. (1996) Cellular Immunology 167:99-107; Lilliehöök, Johannisson, and Håkansson. Expression of adhesion and Fcgamma-receptors on canine blood eosinophils and neutrophils studied by anti-human monoclonal antibodies. Vet Immunol Immunopathol. (1998) 61:181-93; Soergel, MacEwen, Vail, Potter, Sondel, and Helfand. The immunotherapeutic potential of activated canine alveolar macrophages and antitumor monoclonal antibodies in metastatic canine melanoma. J. Immunother. (1999) 22:4 43-53; Phillips, Padilla, Dickerson, Lindstrom, and Helfand. Immunostimulatory effects of human recombinant interleukin-12 on peripheral blood mononuclear cells from normal dogs. Vet Immunol Immunopathol. (1999) 70:189-201; Sato, Teshima, Nakamura, Takagi, Sasaki, Sawada, and Kitani Canine mast cell activation via human IgG1 and IgG4. Int Arch Allergy Immunol. (2004) 135:154-60). Alternatively, the effector cells may be isolated from a native source, e.g., from blood or PBMCs, including cells cultured from blood or fractions thereof, or may be permanent cell lines.

With respect to the neonatal receptor (FcRn), this receptor is unique as it is responsible for the maintenance of serum IgG levels (reviewed in Ghetie and Ward, Multiple roles for the major histocompatibility complex class I-related receptor FcRn, Annu Rev Immunol (2000) 18 739-766; Simister and Mostov An Fc receptor structurally related to MHC class I antigens, Nature 337 (1989), 184-187). FcRn binds IgG in a pH-dependent manner (binding occurs at pH 6.0, but not at pH 7.4) and consists of a heterodimer of an integral membrane glycoprotein, similar to MHC class I α-chains, and β2-microglobulin. FcRn also binds albumin and prolongs its half-life in a concentration-dependent manner similar to IgG (Rodewald, R, pH-dependent binding of immunoglobulins to intestinal cells of the neonatal rat, J Cell Biol 71 666-669, 1976; Chaudhury, Mehnaz, Robinson, Hayton, Pearl and Roopenian et al. The major histocompatibility complex-related Fc receptor for IgG (FcRn) binds albumin and prolongs its lifespan, The Journal of Experimental Medicine 197 (2003), 315-322; Kim, Bronson, Hayton, Radmacher, Roopenian and Robinson et al., Albumin turnover: FcRn-mediated recycling saves as much albumin from degradation as the liver produces, Am J Physiol Gastrointest Liver Physiol (2005)).

Expression of FcRn in several species like possum, swine, cow, sheep and human has been demonstrated (Clanga, Medesan, Richardson, Ghetie and Ward, Identification and function of neonatal Fc receptor in mammary gland of lactating mice, Eur J Immunol 29 (1999) 2515-2523; Adamski, King and Demmer, Expression of the Fc receptor in the mammary gland during lactation in the marsupial *Trichosurus vulpecula* (brushtail possum), Mol Immunol 37 (2000), pp. 435; Schnulle and Hurley, Sequence and expression of the FcRn in the porcine mammary gland, Vet Immunol Immunopathol 91 (2003), 227-231; Kacskovics, Wu, Simister, Frenyo and Hammarstrom, Cloning and characterization of the bovine MHC class I-like Fc receptor, J Immunol 164 (2000), pp. 1889-1897; Mayer, Zolnai, Frenyo, Jancsik, Szentirmay and Hammarstrom et al., Localization of the sheep FcRn in the mammary gland, Vet Immunol Immunopathol 87 (2002), pp. 327-330; Mayer, Doleschall, Bender, Bartyik, Bosze and Frenyo et al. Expression of the neonatal Fc receptor (FcRn) in the bovine mammary gland, J Dairy Res 72 (2005) (Spec No: 107-112); Clanga, Clanga, Cozma, Ward and Carasevici, The MHC class I related Fc receptor, FcRn, is expressed in the epithelial cells of the human mammary gland, Hum Immunol 64 (2003), pp. 1152-1159; Mayer, Zolnai, Frenyo, Jancsik, Szentirmay and Hammarstrom et al., Redistribution of the sheep neonatal Fc receptor in the mammary gland around the time of parturition in ewes and its localization in the small intestine of neonatal lambs, Immunology 107 (2002), 288-296).

The recombinant polypeptide composition of the present invention includes one or more antibody variable domains or fragment thereof having any specificity, and is preferably an antibody variable domain or fragment thereof which recognizes a tumor-related antigen, an allergy- or inflammation-related antigen, a cardiovascular disease-related antigen, an autoimmune disease-related antigen or a viral or bacterial infection-related antigen, or a tumor-related antigen.

The invention disclosed herein further contemplates the therapeutic use of the recombinant polypeptide, or fragments, derivatives, or modifications thereof, for the purpose of treating, preventing, reducing or otherwise lowering (e.g., by at least 10%, 20%, 30%, 40%, 50%, 60%, 70%, 80%, 90% or more) disease conditions associated or mediated by inflammation.

In one embodiment, the recombinant polypeptides, or fragments, derivatives, or modifications thereof, are specifically administered to a patient. In another embodiment, the recombinant polypeptide of the invention, or fragments, derivatives, or modifications thereof, are introduced into cells and/or a tissue while under in vitro or ex vivo conditions, prior to the transplantation of the cells and/or a tissue into a mammalian organism for the purpose of treating, preventing, reducing or otherwise lowering disease conditions or symptoms associated or mediated by inflammation.

Further envisioned within the scope of this invention is the use of a recombinant nucleic acids or proteins, or fragments or derivatives thereof, for the treatment of all companion animal diseases and/or conditions that are mediated or associated with the onset of inflammation, as well as companion animal diseases and/or conditions that are mediated or associated with autoimmunity. Such diseases and/or conditions are referred to herein as inflammatory disorders and include but are not restricted to inflammation, autoimmune disease and immune-mediated.

The term "cytokine" refers to all mammalian, preferably from companion animals, cytokines that bind extracellular receptors upon the cell surface and thereby modulate cell function, including but not limited to IL-1, IL-4, IL-6, IL-18, TNF-A, and IFN-gamma. Cytokines are released by cells of the immune system and act as intracellular modulators in the generation of an immune response. Also included in this definition are chemokines. The term "chemokine" refers to chemotactic cytokines expressed within mammalian organisms that mediate the recruitment and infiltration of leukocytes into tissues. The term "chemokine" includes but is not limited to all mammalian members of the C, CC, CXC, and CXXXC families of chemotactic cytokines, classified within the art based upon the distribution of cysteine residues therein. The term "chemokine receptor" refers to transmembrane proteins to interact with one or more chemokines.

The term "cytokine receptor" refers to all mammalian, preferably human, cytokine receptors within the art that bind one or more cytokine(s), including but not limited to receptors of IL-1, IL-4, IL-6, IL-18, TNF-.alpha. The term "chemokine receptor" shall include but is not limited to all chemokine receptors classified within the art as CR, CCR, CXCR and CXXXCR.

The terms "fragment" or "region" refer to a portion of a polypeptide or nucleic acid molecule that contains, preferably, at least 10%, 20%, 30%, 40%, 50%, 60%, 70%, 80%, 90%, 95%, or more of the entire length of the reference nucleic acid molecule or polypeptide.

The term "heterologous" refers to any two or more nucleic acid or polypeptide sequences that are not normally found in the same relationship to each other in nature. For instance, a heterologous nucleic acid is typically recombinantly produced, having two or more sequences, e.g., from unrelated genes arranged to make a new functional nucleic acid, e.g., a promoter from one source and a coding region from another source. Similarly, a heterologous polypeptide will often refer to two or more subsequences that are not found in the same relationship to each other in nature (e.g., a fusion protein).

The term "homolog" refers to a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 55%, 57%, 60%, 65%, 68%, 70%, more preferably 80% or 85%, and most preferably 90%, 95%, 98%, or 99% identical at the amino acid level or nucleic acid to a reference sequence.

The term "isolated" in reference to a protein or nucleic acid or sequence or fragment thereof means isolated from its native environment, and it is this understood that the isolated protein or nucleic acid or sequence or fragment thereof may be replicated and incorporated into a non-native environment. For example a nucleic acid sequence isolated from its natural source, which is replicated and used to transform a cell, may still be referred to as "isolated" from its native environment, although it is not physically the same material taken from the original source (e.g., having been replicated in vitro) and is not separate from other nucleic acid (being incorporated into the transformed cell).

The term "recombinant" in reference to a protein or nucleic acid refers to a protein or nucleic acid which is the product genetic engineering, in which DNA sequences which would not come together naturally are combined. Unless otherwise stated, it is not intended to refer to naturally occurring recombination.

"Caninized" forms of non-canine antibodies are chimeric antibodies which contain minimal sequence derived from non-canine antibody. For the most part, caninized antibodies are canine antibody (acceptor or recipient antibody) in which hypervariable region residues of the recipient are replaced by hypervariable region residues from a non-canine species (donor antibody) such as mouse, rat, rabbit, cat, dogs, goat, chicken, bovine, horse, llama, camel, dromedaries, sharks, non-human primates, human, humanized, recombinant sequence, or an engineered sequence having the desired properties. In some instances, framework region (FR) residues of the canine antibody are replaced by corresponding non-canine residues. Furthermore, caninized antibodies may comprise residues which are not found in the recipient antibody or in the donor antibody. These modifications are made to further refine antibody performance. The caninized antibody may also comprise at least a portion of an immunoglobulin constant region (Fc) of a canine antibody.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived from.

As used herein, the term "not immunogenic" means that the antibody does not raise an antibody response of sufficient magnitude to reduce the effectiveness of continued administration of the antibody in the majority of treated patients for sufficient time to achieve therapeutic efficacy.

As used herein, the term "therapeutic" encompasses the full spectrum of treatments for a disease or disorder. A "therapeutic" agent of the invention may act in a manner that is prophylactic or preventive, including those that incorporate procedures designed to target individuals that can be identified as being at risk (pharmacogenetics); or in a manner that is ameliorative or curative in nature; or may act to slow the rate or extent of the progression of a disease or disorder; or may act to minimize the time required, the occurrence or extent of any discomfort or pain, or physical limitations associated with recuperation from a disease, disorder or physical trauma; or may be used as an adjuvant to other therapies and treatments.

"Treatment" refers to both therapeutic treatment and prophylactic or preventative measures. Those in need of treatment include those already with the disorder as well as those in which the disorder is to be prevented.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a chemotherapeutic agent and an antibody. Alternatively, a combination therapy may involve the administration of an antibody and/or one or more chemotherapeutic agents, alone or together with the delivery of another treatment, such as radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending veterinarian or attending caregiver.

The term "monotherapy" refers to a treatment regimen based on the delivery of one therapeutically effective compound, whether administered as a single dose or several doses over time.

A "chimeric antibody" comprises a sequence of the constant domain region or fragment thereof from a target species and the variable domain from the donor species fused to the constant domain of the target species.

Antibodies (mAbs) that can be subjected to the techniques set forth herein include monoclonal and polyclonal mAbs, and antibody fragments such as Fab, Fab', F(ab')2, Fd, scFv, diabodies, antibody light chains, antibody heavy chains and/or antibody fragments derived from various sources. An antibody is obtained from a sequence donor species. More particularly, the nucleic acid or amino acid sequence of the variable portion of the light chain, heavy chain or both, of the donor species antibody has specificity for a desired antigen. The donor species is any species which was used to generate the antibodies or antibody libraries, e.g., mouse, rat, rabbit, cat, dogs, goat, chicken, bovine, horse, llama, camel, dromedaries, sharks, non-human primates, human, humanized, recombinant sequence, engineered sequence, etc. Techniques for generating and cloning monoclonal antibodies are well known to those skilled in the art.

After sequencing the constant domains from the heavy chain and the light chains, kappa or lambda, the regions are separated into discrete regions using any published definition of domains (e.g., Kabat, Chothia, AbM, contact definition and any combination thereof, and any others known to those skilled in the art).

With respect to the constant domains of light chains, a constant domain or fragment thereof from the target species belonging to the lambda light chain or kappa light chain type, or the constant domain or fragment thereof from the target species belonging to the lambda light chain type may be fused to the light chain variable domains. It is contemplated that the polypeptide could comprise a constant domain region fused together with a polypeptide other than an antibody.

With respect to the constant domains of heavy chains, a constant domain or fragment thereof of any subclass from the target species may be fused to the heavy chain variable domains.

With respect to the pairing of the constant domain from the heavy chain and the constant domain from the light chain, any combination can be made.

The constant domain region of the method disclosed herewith can be isolated from an IgG, IgM, IgD, IgE, IgA, lambda, or kappa antibody. In some embodiments, the antibody is an IgG antibody. The donor species antibody constant domain sequence can be, for example, from a canine antibody, a feline antibody, an equine antibody or a human antibody.

The engineering of the recombinant polypeptide of the claimed invention can be created by introducing modifications, additions or deletions to a nucleic acid encoding the antibody can be introduced by a method comprising recombination, error-prone PCR, shuffling, oligonucleotide-directed mutagenesis, assembly PCR, sexual PCR mutagenesis, in vivo mutagenesis, site-specific mutagenesis, gene reassembly, synthetic ligation reassembly or a combination thereof.

In a further aspect, the invention includes pharmaceutical compositions in which antibody constant domain regions of the present invention are fused to a polypeptide and are provided for therapeutic or prophylactic uses. The invention features a method for treating a dog subject having a particular antigen, e.g., one associated with disease. The method includes administering a therapeutically effective amount of a recombinant antibody specific for the particular antigen, with the recombinant antibody described herein.

The amount of polypeptide containing the antibody constant domain regions of the present invention useful to produce a therapeutic effect can be determined by standard techniques well known to those of ordinary skill in the art. The polypeptide will generally be provided by standard technique within a pharmaceutically acceptable buffer, and may be administered by any desired route. The route of administration of the polypeptide of the invention may be oral, parenteral, by inhalation or topical. The term parenteral as used herein includes intravenous, intramuscular, subcutaneous, rectal, vaginal or intraperitoneal administration.

Polypeptides produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, apoptosis, or complement fixation. Such polypeptides may be used as passive or active therapeutic agents against a number of diseases, including B cell lymphoma, T cell lymphoma, autoimmune diseases, inflammatory diseases, infectious diseases, and transplantation.

In one embodiment of the above aspects, the antigen is a tumor antigen, an antigen involved in an immune disorder, an antigen involved in an autoimmune response, a receptor expressed on a host cell or available in blood circulation or secreted by a cell and the recombinant antibody is able to either deplete undesired cells or to block or stimulates receptor functions, or neutralizes active soluble products.

The recombinant polypeptide (or fragments thereof) of this invention may be useful for treating tumors in companion animals. More specifically, they may be useful for reducing tumor size, inhibiting tumor growth and/or prolonging the survival time of tumor-bearing animals. Accordingly, this invention also relates to a method of treating tumors in a dog or other animals by administering an effective dose. An effective dose is expected to be in the range of about 0.05 to 100 milligrams per kilogram body weight per day.

The invention thus provides in a first embodiment: Recombinant Protein 1, a recombinant protein (e.g., a recombinant antibody or soluble receptor) having (i) a binding domain capable of specific binding to an epitope (for example an antibody variable domains, a receptor, a growth factor, a cytokine, or a fragment of any of the foregoing which is capable of specifically binding the desired epitope) and (ii) an effector domain comprising a constant domain region which is derived from immunoglobulin of a first species which is a companion mammal, e.g. dog, cat, or horse, having engineered substitutions at one or more positions and having an altered interaction with one or more FcRs or other ligands, and optionally enhanced effector function, relative to the parent constant domain region; for example 1.1 The recombinant protein, wherein the effector domain is from a domain of IgA, IgD, IgG, IgE and IgM, and the flexible hinge N-terminal to these domains.

1.2 Any of the foregoing recombinant proteins, wherein the region or fragment has altered interaction with one or more FcRs or other ligands, and optionally enhanced effector function, relative to the parent constant domain region 1.3 Any of the foregoing recombinant proteins wherein the effector domain is from a domain of IgG, IgM, IgD, IgE, IgA, lambda or kappa antibody.

1.4 Any of the foregoing recombinant proteins, wherein the binding domain is a variable domain or fragment of an antibody.

1.5 Any of the foregoing recombinant proteins, wherein the binding domain specifically binds to a tumor-related antigen.

1.6 Any of the foregoing recombinant proteins, wherein the binding domain specifically binds to an allergy or inflammation related antigen.

1.7 Any of the foregoing recombinant proteins, wherein the binding domain specifically binds to a cardiovascular disease-related antigen.

1.8 Any of the foregoing recombinant proteins, wherein the binding domain specifically binds to an autoimmune disease-related antigen.

1.9 Any of the foregoing recombinant proteins, wherein the binding domain specifically binds to a viral or bacterial infection-related antigen.

1.10 Any of the foregoing recombinant proteins, wherein the binding domain specifically binds to a tumor-related antigen.

1.11 Any of the foregoing recombinant proteins, wherein the binding domain specifically binds to proteins, subunits, domains, motifs, and/or epitopes selected from the group consisting of: 17-IA, 4-1BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, Artemin, anti-Id, ASPARTIC, Atrial natriuretic factor, av/b3 integrin, Axl, b2M, B7-1, B7-2, B7-H, B-lymphocyte Stimulator (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMPs, b-NGF, BOK, Bombesin, Bone-derived neurotrophic factor, BPDE, BPDE-DNA, BTC, complement factor 3 (C3), C3a, C4, C5, C5a, C10, CA125, CAD-8, Calcitonin, cAMP, carcinoembryonic antigen (CEA), carcinoma-associated antigen, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CC1, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 proteins), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, *Clostridium botulinum* toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor-associated antigen, DAN, DCC, DcR3, DC-SIGN, Decay accelerating factor, des(1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, Enkephalinase, eNOS, Eot, eotaxin1, EpCAM, Ephrin B2/EphB4, EPO, ERCC, E-selectin, ET-1, Factor IIa, Factor VII, Factor VIIIc, Factor IX, fibroblast activation protein (FAP), Fas, FcR1, FEN-1, Ferritin, FGF, FGF-19, FGF-2, FGF3, FGF-8, FGFR, FGFR-3, Fibrin, FL, FLIP, Flt-3, Flt-4, Follicle stimulating hormone, Fractalkine, FZD1, FZD2, FZD3, FZD4, FZD5, FZD6, FZD7, FZD8, FZD9, FZD10, G250, Gas 6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (Myostatin), GDF-9, GDF-15 (MIC-1), GDNF, GDNF, GFAP, GFRa-1, GFR-alpha1, GFR-alpha2, GFR-alpha3, GITR, Glucagon, Glut 4, glycoprotein IIb/IIIa (GP IIb/IIIa), GM-CSF, gp130, gp72, GRO, Growth hormone releasing factor, Hapten (NP-cap or NIP-cap), HB-EGF, HCC, HCMV gB envelope glycoprotein, HCMV) gH envelope glycoprotein, HCMV UL, Hemopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, High molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding proteins, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, Inhibin, iNOS, Insulin A-chain, Insulin B-chain, Insulin-like growth factor 1, integrin alpha2, integrin alpha3, integrin alpha4, integrin alpha4/beta1, integrin alpha4/beta7, integrin alpha5 (alphaV), integrin alpha5/beta1, integrin alpha5/beta3, integrin alpha6, integrin beta1, integrin beta2, interferon gamma, IP-10, I-TAC, JE, Kallikrein 2, Kallikrein 5, Kallikrein 6, Kallikrein 11, Kallikrein 12, Kallikrein 14, Kallikrein 15, Kallikrein L1, Kallikrein L2, Kallikrein L3, Kallikrein L4, KC, KDR, Keratinocyte Growth Factor (KGF), laminin 5, LAMP, LAP, LAP (TGF-1), Latent TGF-1, Latent TGF-1 bp1, LBP, LDGF, LECT2, Lefty, Lewis-Y antigen, Lewis-Y related antigen, LFA-1, LFA-3, Lfo, LIF, LIGHT, lipoproteins, LIX, LKN, Lptn, L-Selectin, LT-a, LT-b, LTB4, LTBP-1, Lung surfactant, Luteinizing hormone, Lymphotoxin Beta Receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC(HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Muellerian-inhibitin substance, Mug, MuSK, NAIP, NAP, NCAD, N-Cadherin, NCA 90, NCAM, NCAM, Neprilysin, Neurotrophin-3, -4, or -6, Neurturin, Neuronal growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, Parathyroid hormone, PARC, PARP, PBR, PBSF, PCAD, P-Cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, Proinsulin, Prorelaxin, Protein C, PS, PSA, PSCA, prostate specific membrane antigen (PSMA), PTEN, PTHrp, Ptk, PTN, R51, RANK, RANKL, RANTES, RANTES, Relaxin A-chain, Relaxin B-chain, renin, respiratory syncytial virus (RSV) F, RSV Fgp, Ret, Rheumatoid factors, RLIP76, RPA2, RSK, S100, SCF/KL, SDF-1, SERINE, Serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptors (e.g., T-cell receptor alpha/beta), TdT, TECK, TEM1, TEM5, TEM7, TEM8, TERT, testicular PLAP-like alkaline phosphatase, TfR, TGF, TGF-alpha, TGF-beta, TGF-beta Pan Specific, TGF-beta R1 (ALK-5), TGF-beta R11, TGF-beta RIIb, TGF-beta RIII, TGF-beta1, TGF-beta2, TGF-beta3, TGF-beta4, TGF-beta5, Thrombin, Thymus Ck-1, Thyroid stimulating hormone, Tie, TIMP, TIQ, Tissue Factor, TMEFF2, Tmpo, TMPRSS2, TNF, TNF-alpha, TNF-alpha beta, TNF-beta2, TNFc, TNF-RI, TNF-RII, TNFRSF10A (TRAIL R1Apo-2, DR4), TNFRSF10B (TRAIL R2DR5, KILLER, TRICK-2A, TRICK-B), TNFRSF10C (TRAIL R3DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF R1CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3M68, TR6), TNFRSF7 (CD27), TNFRSF8 (CD30), TNFRSF9 (4-1BB CD137, ILA), TNFRSF21 (DR6), TNFRSF22 (DCTRAIL R2 TNFRH2), TNFRST23 (DCTRAIL R1TNFRH1), TNFRSF25 (DR3Apo-3, LARD, TR-3, TRAMP, WSL-1), TNFSF10 (TRAIL Apo-2 Ligand, TL2), TNFSF11 (TRANCE/RANK Ligand ODF, OPG Ligand), TNFSF12 (TWEAK Apo-3 Ligand, DR3Ligand), TNFSF13 (APRIL TALL2), TNFSF13B (BAFF BLYS, TALL1, THANK, TNFSF20), TNFSF14 (LIGHT HVEM Ligand, LTg), TNFSF15 (TL1A/VEGI), TNFSF18 (GITR Ligand AITR Ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 Ligand gp34, TXGP1), TNFSF5 (CD40 Ligand CD154, gp39, HIGM1, IMD3, TRAP), TNFSF6 (Fas Ligand Apo-1 Ligand, APT1 Ligand), TNFSF7 (CD27 Ligand CD70), TNFSF8 (CD30 Ligand CD153), TNFSF9 (4-1BB Ligand CD137 Ligand), TP-1, t-PA, Tpo, TRAIL, TRAIL R, TRAIL-R1, TRAIL-R2, TRANCE, transferring receptor, TRF, Trk, TROP-2, TSG, TSLP, tumor-associated antigen CA 125, tumor-associated antigen expressing Lewis Y related carbohydrate, TWEAK, TXB2, Ung, UPAR, uPAR-1, Urokinase, VCAM, VCAM-1, VECAD, VE-Cadherin, VE-cadherin-2, VEFGR-1 (fit-1), VEGF, VEGFR, VEGFR-3 (flt-4), VEGI, VIM, Viral antigens, VLA, VLA-1, VLA-4, VNR integrin, von Willebrands factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, and receptors for hormones and growth factor.

1.12 Any of the foregoing recombinant proteins, wherein the binding domain is a receptor or fragment thereof.

1.13 The recombinant protein of 1.12, wherein the binding domain is a growth factor, or a fragment thereof.

1.14 Any of the foregoing recombinant proteins, wherein the effector domain has an altered interaction with one or more FcRs or other ligands, and optionally enhanced effector function relative to the parent constant domain region, 1.15 Any of the foregoing recombinant proteins 1-1.13, wherein the effector domain has decreased binding to one or more receptors for improved therapeutic effect.

1.16 Any of the foregoing recombinant proteins, for treatment, prophylaxis, reduction or otherwise lowering of disease conditions associated or mediated by inflammation, or an inflammatory disorder.

1.17 The recombinant protein of 1.16, wherein the inflammatory disorder is selected from the group consisting of: of acute inflammation, rheumatoid arthritis, transplant rejection, transplant vasculopathy, asthma, allergic inflammation, restenosis, arterial restenosis, by-pass graft occlusion, inflammatory bowel disease, uveitis, multiple sclerosis, psoriasis, wound healing, lupus erythematosus, allergic rhinitis, atopic dermatitis, food allergies, type 1 insulin-dependent diabetes mellitus, dermatitis, meningitis, thrombotic thrombocytopenic purpura, encephalitis, leukocyte adhesion deficiency, rheumatic fever, psoriatic arthritis, osteoarthritis, ocular inflammatory disorders, progressive systemic sclerosis, primary biliary cirrhosis, pemphigus, pemphigoid, necrotizing vasculitis, myasthenia gravis, polymyositis, sarcoidosis, granulomatosis, vasculitis, pernicious anemia, CNS inflammatory disorder, antigen-antibody complex mediated diseases, autoimmune hemolytic anemia, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis, pemphigus vulgaris, Behcet's syndrome, acute respiratory distress syndrome (ARDS), ischemic heart disease, atherosclerosis, post-dialysis syndrome, leukemia, acquired immune deficiency syndrome, septic shock, lipid histiocytosis, and cancer.

1.18 Any of the foregoing recombinant proteins, wherein the binder region comprises an antibody hypervariable region consists essentially of residues corresponding to an antibody from a second species which is different from the first species.

1.19 Any of the foregoing recombinant proteins, wherein effector domain comprises a lambda light chain or kappa light chain.

1.20 Any of the foregoing recombinant proteins, wherein effector domain comprises a lambda light chain and is fused to a light chain variable domain.

In a particular embodiment, the recombinant proteins are heterochimeric antibodies and/or fragments thereof comprising (i) hypervariable region sequences wholly or substantially corresponding to sequences found in antibodies from a donor species (e.g., a mouse or rat); (ii) constant region sequences wholly or substantially corresponding to sequences found in antibodies from a target species (a companion animal) which is different from the donor species, (the constant region in this case having been selected to provide the enhanced effector function as herein described); and (iii) heavy and/or light chain variable framework sequences which contain at least three, e.g. at least four, or at least five, or at least six contiguous non-CDR residues corresponding to sequences found in antibodies from a target species and at least three, e.g. at least four, or at least five, or at least six contiguous non-CDR residues corresponding to sequences found in antibodies from a donor species. Heterochimeric antibodies include heterochimeric hybrid antibodies wherein the target antibody sequences are from different antibodies from the target species. In one embodiment, the heterochimeric antibody comprises FR1 and/or FR4 variable region sequences wholly or substantially corresponding to FR1 and/or FR4 variable region sequences found in antibodies from a target species, and CDR, FR2 and FR3 sequences wholly or substantially corresponding to sequences found in the donor species antibody. Heterochimeric antibodies are more fully described in our co-pending applications U.S. Ser. No. 12/584,390 and PCT/US2009/04997, the contents of which are incorporated herein by reference.

In a second embodiment, the invention provides a method of treatment (Method 2) comprising providing an effective amount of a recombinant protein of any of the embodiments of 1.1-1.20 to a companion animal, e.g., a dog, cat or horse, for example, to treat any of the diseases or conditions identified in 1.16 or 1.17, optionally in a regimen of combination therapy with the second therapeutic agent, e.g. a chemotherapeutic agent.

In a third embodiment, the invention provides a veterinary pharmaceutical composition comprising a recombinant protein of any of the embodiments of 1.1-1.20

The invention further provides recombinant proteins which comprise:

An amino acid sequence, e.g. isolated from canine spleen or peripheral blood, comprising one or more of the following: SEQ ID NO:1, SEQ ID NO: 2, SEQ ID NO: 3, SEQ ID NO: 4, SEQ ID NO: 5, SEQ ID NO: 6, and SEQ ID NO: 7;

An amino acid sequence, e.g., isolated from a canine constant domain region of kappa light chain, comprising: SEQ ID NO:8; and/or An amino acid sequence, e.g., isolated from a canine constant domain region of lambda light chain, comprising: SEQ ID NO: 9;

or

An amino acid sequence, e.g., from a feline constant domain region isolated from feline spleen or peripheral blood cells, comprising a sequence selected from SEQ ID NOS: 10-21;

and nucleic acid encoding such recombinant proteins.

In a further embodiment, the invention comprises a method (Method 3) of engineering an antibody for use in treating a companion animal, e.g., a dog, cat or horse (e.g., for use in Method 2 supra), comprising:

a. Isolating spleen cells or peripheral blood mononuclear cells from the species to be treated;

b. Making cDNA in said cells and amplifying the cDNA encoding the antibody constant domains from said cells;

c. Transforming a host cell with an expression vector comprising cDNA for the constant domain together with DNA encoding a variable region having affinity for an epitope;

d. Expressing and retrieving antibody from the host cell thus transformed, and e. Assessing the effector function of the constant regions of antibodies thus obtained, i. by directly assessing the binding of the antibody to Fc; and/or ii. by assessing the ability of the antibody to kill a target cell, wherein the variable region of the antibody recognizes an epitope on the target cell, in the absence of complement (ADCC) and/or presence of complement (CDC);

f. Selecting a constant region having the desired effector function.

Example 1

Fc Receptors

Cloning and Expression of the Fc Receptors

The canine DNA sequences (*Canis familiaris*) are predicted by automated computational analysis and derived from annotated genomic sequence using gene prediction method: GNOMON supported by EST evidence. These sequences, when translated, show regions of variable homology with previously identified Fc protein sequences. These sequences are cloned by amplifying the coding regions or fragments thereof. Signal sequences may be added for expression amplification purposes.

Secreted versions of recombinant Fc receptors are engineered by replacing their C-terminal transmembrane domains with 6×His sequences and using a signal peptide as a signal sequence. The Fc gamma receptor sequences are subcloned into pcDNA3 (Invitrogen). After transfection into mammalian cells, the soluble recombinant protein is released into the supernatants. Supernatants are used to test the binding to the recombinant polypeptides containing a constant domain region or fragment thereof. The soluble recombinant protein is either purified from the supernatant utilizing nickel affinity chromatography or by affinity chromatography using an antibody to the receptor.

A set of FC receptors GenBank accession numbers is listed below: dFcgRI (NW_139881), dFcgRII (NW_139918), dFcgRIII (NW_139918), dFceRI (NW_139918), dFcrla (NW_139918), dFcrlb (NW_139918), dFcrl1 (NW_139860), dFcrl2 (NW_139860), dFcrl3 (NW_139860), dFcrl4 (NW_139860), dFcrl5 (NW_139860), dFcrl6 (NW_139918), dFcrls (NW_139860), dCD5L (NW_139860), FcRn (XP_533618).

Example 2

Cloning of the Canine Constant Domain Regions

I. Cloning of the Heavy Chain and Light Chain

Heavy chain and light chain sequences were cloned from peripheral blood mononuclear cells (PBMC). Total RNA was extracted from 1 million canine peripheral blood (PBMC) using the MasterPure™ RNA Purification Kit (Epicentre Biotechnology, Cat. No. MCR85102). The first-strand cDNA was synthesized from 2 μg of total RNA using SuperScript, First-Strand Synthesis, System for RT-PCR kit (Invitrogen, Catalog No. 11904-018) according to the manufacturer's instructions. Reactions are terminated by heating at 70° C. for 15 min. The coding region or fragment thereof was then amplified by PCR using the primers listed below. The PCR reactions were as follows: 1 μl total RNA, 2.5 μl of 10×Pfx buffer, 2 μl dNTP (2.5 mM each), 1 μl forward primer at 10 μM, 1 μl reverse primer at 10 μM, 16.5 μl H$_2$O, 1 μl polymerase Platinum® Pfx DNA (Invitrogen, Catalog No. 11904-018). The samples were denatured at 94° C. for 5 min followed by amplifications for 35 cycles (94° C. for 30 s, 62° C. for 20 s, 72° C. for 45 s). The negative controls contained all the reagents except cDNA or all the reagents except one of the two primers. The PCR products were cloned into the pBluescript derived vector (Stratagene) or pcDNA 3.1 (Invitrogen) and sequenced to verify PCR specificity.

| Region for Amplification | Primer Designation | Primer Sequence |
| --- | --- | --- |
| HC Constant Domain - Full Length | HC-Forward<br>HC-Reverse | 5'-GCCTCCACCACGGCCCC-3'<br>5'-TCATTTACCCGGAGAATGGG-3' |
| Lambda LC Constant Domain - Full Length | L-LC-Forward<br>L-LC-Reverse | 5'-GGTCAGCCCAAGGCCWMCC-3'<br>5'-CTAAGAGCACTCTGCRGGG-3' |
| Kappa LC Constant Domain - Full Length | K-LC-Forward<br>K-LC-Reverse | 5'-AATGATGCCCAGCCAGCCG-3'<br>5'-TTAGTCCACTCTCTGACACTC-3' |
| 3'-end Universal Primer | Poly dTT | 5'-TTTTTTTTTTTTTTTTTTTT-3' |

II. Heavy Chains and Light Chains Constant Domain Regions Sequences

The amino acid sequences of the heavy chain constant domain regions from independent PBMC samples are listed below.

The multiple sequence alignment of the heavy chain constant domain regions described above is illustrated in Table 2. The putative CH1, CH2, CH3 domains and the hinge region between CH1 and CH2 are indicated. The first amino acid residue of each putative domain is underlined. Sequence identity is marked with an asterisk.

TABLE 1

Amino acid sequence of the recombinant canine heavy chain constant domains.

SEQ ID NO: 1   VET 200
ASTTAPSVFPLAPSCGSQSGSTVALACLVSGYIPEPVTVSWNSGSLTSGVHTFPSILQSS
GLYSLSSMVTVPSSRWPSETFTCNVAHPATNTKVDKPVVKECECKCNCNNCPCPGCGLLG
GPSVFIFPPKPKDILVTARTPTVTCVVVDLDPENPEVQISWFVDSKQVQTANTQPREEQS
NGTYRVVSVLPIGHQDWLSGKQFKCKVNNKALPSPIEEIISKTPGQAHQPNVYVLPPSRD
EMSKNTVTLTCLVKDFFPPEIDVEWQSNGQQEPESKYRMTPPQLDEDGSYFLYSKLSVDK
SRWQRGDTFICAVMHEALHNHYTQKSLSHSPGK

SEQ ID NO: 2   VET 201
ASTTAPSVFPLAPSCGSQSGSTVALACLVSGYFPEPVTVSWNSGSLTSGVHTFPSVLQSS
GLYSLSSMVTVPSSRWPSETFTCNVAHPASKTKVDKPVPKRENGRVPRPPDCPKCPAPEM
LGGPSVFIFPPKPKDTLLIARTPEVTCVVVDLDPEDPEVQISWFVDGKQMQTAKTQPREE
QFNGTYRVVSVLPIGHQDWLKGKQFTCKVNNKALPSPIERTISKARGQAHQPSVYVLPPS
REELSKNTVSLTCLIKDFFPPDIDVEWQSNGQQEPESKYRTTPPQLDEDGSYFLYSKLSV
DKSRWQRGDTFICAVMHEALHNHYTQKSLSHSPGK

SEQ ID NO: 3   VET 202
ASTTAPSVFPLAPSCGSTSGSTVALACLVSGYFPEPVTVSWNSGSLTSGVHTFPSVLQSS
GLYSLSSMVTVPSSRWPSETFTCNVAHPASKTKVDKPVPKRENGRVPRPPDCPKCPAPEM
LGGPSVFIFPPKPKDTLLIARTPEVTCVVVDLDPEDPEVQISWFVDGKQMQTAKTQPREE
QFNGTYRVVSVLPIGHQDWLKGKQFTCKVNNKALPSPIERTISKARGQAHQPSVYVLPPS
REELSKNTVSLTCLIKDFFPPDIDVEWQSNGQQEPESKYRTTPPQLDEDGSYFLYSKLSV
DKSRWQRGDTFICAVMHEALHNHYTQKSLSHSPGK

SEQ ID NO: 4   VET 203
ASTTAPSVFPLAPSCGSTSGSTVALACLVSGYFPEPVTVSWNSGSLTSGVHTFPSVLQSS
GLYSLSSMVTVPSSRWPSETFTCNVAHPASKTKVDKPVPKRENGRVPRPPDCPKCPAPEM
LGGPSVFIFPPKPKDTLLIARTPEVTCVVVDLDPEDPEVQISWFVDGKQMQTAKTQPREE
QFNGTYRVVSVLPIGHQDWLKGKQFTCKVNNKALPSPIERTISKARGQAHQPSVYVLPPS
REELSKNTVSLTCLIKDFFPPDIDVEWQSNGQQEPESKYRTTPPQLDEDGSYFLYSKLSV
DKSRWQRGDTFICAVMHEALHNHYTQKSLSHSPGK

SEQ ID NO: 5   VET 204
ASTTAPSVFPLAPSCGSTSGSTVALACLVSGYFPEPVTVSWNSGSLTSGVHTFPSVLQSS
GLYSLSSMVTVPSSRWPSETFTCNVAHPASKTKVDKPVPKRENGRVPRPPDCPKCPAPEM
LGGPSVFIFPPKPKDTLLIARTPEVTCVVVDLDPEDPEVQISWFVDGKQMQTAKTQPREE
QFNGTYRVVSVLPIGHQDWLKGKQFTCKVNNKALPSPIERTISKARGQAHQPSVYVLPPS
REELSKNTVSLTCLIKDFFPPDIDVEWQSNGQQEPESKYRTTPPQLDEDGSYFLYSKLSV
DKSRWQRGDTFICAVMHEALHNHYTQKSLSHSPGK

SEQ ID NO: 6   VET 205
ASTTAPSVFPLAPSCGSQSGSTVALACLVSGYIPEPVTVSWNSGSLTSGVHTFPSILQSS
GLYSLSSMVTVPSSRWPSETFTCNVAHPATNTKVDKPVVKECECKCNCNNCPCPGCGLLG
GPSVFIFPPKPKDILVTARTPTVTCVVVDLDPENPEVQISWFVDGKQMQTAKTQPREEQF
NGTYRVVSVLPIGHQDWLKGKQFTCKVNNKALPSPIERTISKARGQAHQPSVYVLPPSRE
ELSKNTVSLTCLIKDFFPPDIDVEWQSNGQQEPESKYRTTPPQLDEDGSYFLYSKLSVDK
SRWQRGDTFICAVMHESLHNHYTQKSLSHSPGK

SEQ ID NO: 7   VET 206
ASTTAPSVFPLAPSCGSTSGSTVALACLVSGYFPEPVTVSWNSGSLTSGVHTYPSVLQSS
GLYSLSSMVTVPSSRWPSETFTCNVAHPASKTKVDKPVPKRENGRVPRPPGCPKCPAPEM
LGGPSVFIFPPKPKDTLLIARTPEVTCVVVDLDPEDPEVQISWFVDSKQVQTANTQPREE
QSNGTYRVVSVLPIGHQDWLSGKQFKCKVNNKALPSPIEEIISKTPGQAHQPNVYVLPPS
RDEMSKNTVTLTCLVKDFFPPEIDVEWQSNGQQEPESKYRMTPPQLDEDGSYFLYSKLSV
DKSRWQRGDTFICAVMHEALHNHYTQKSLSHSPGK

TABLE 2

Amino acid sequence alignment of the recombinant canine heavy chain constant domains.

```
Domains   < ---------------------- CH1 ----------------------------
VET201    ASTTAPSVFPLAPSCGSQSGSTVALACLVSGYFPEPVTVSWNSGSLTSGVHTFPSVLQSS
VET203    ASTTAPSVFPLAPSCGSTSGSTVALACLVSGYFPEPVTVSWNSGSLTSGVHTFPSVLQSS
VET206    ASTTAPSVFPLAPSCGSTSGSTVALACLVSGYFPEPVTVSWNSGSLTSGVHTYPSVLQSS
VET200    ASTTAPSVFPLAPSCGSQSGSTVALACLVSGYIPEPVTVSWNSGSLTSGVHTFPSILQSS
VET205    ASTTAPSVFPLAPSCGSQSGSTVALACLVSGYIPEPVTVSWNSGSLTSGVHTFPSILQSS
Identity  ****************.**************.*******************.**:****

Domains   -------------- CH1 ------------ > <     Hinge    > < -
VET201    GLYSLSSMVTVPSSRWPSETFTCNVAHPASKTKVDKPVPKRENGRVPRPPDCPKCPAPEM
VET203    GLYSLSSMVTVPSSRWPSETFTCNVAHPASKTKVDKPVPKRENGRVPRPPDCPKCPAPEM
VET206    GLYSLSSMVTVPSSRWPSETFTCNVAHPASKTKVDKPVPKRENGRVPRPPGCPKCPAPEM
VET200    GLYSLSSMVTVPSSRWPSETFTCNVAHPATNTKVDKPVVKECECKCNCN-NCP-CPGCGL
VET205    GLYSLSSMVTVPSSRWPSETFTCNVAHPATNTKVDKPVVKECECKCNCN-NCP-CPGCGL
Identity  *****************************.:******* *. : :   .** **. :

Domains   --------------------- CH2 -------------------------------
VET201    LGGPSVFIFPPKPKDTLLIARTPEVTCVVVDLDPEDPEVQISWFVDGKQMQTAKTQPREE
VET203    LGGPSVFIFPPKPKDTLLIARTPEVTCVVVDLDPEDPEVQISWFVDGKQMQTAKTQPREE
VET206    LGGPSVFIFPPKPKDTLLIARTPEVTCVVVDLDPEDPEVQISWFVDSKQVQTANTQPREE
VET200    LGGPSVFIFPPKPKDILVTARTPTVTCVVVDLDPENPEVQISWFVDSKQVQTANTQPREE
VET205    LGGPSVFIFPPKPKDILVTARTPTVTCVVVDLDPENPEVQISWFVDGKQMQTAKTQPREE
Identity  ***************.*:.**** ***********:**********.**:***:******

Domains   ----------------- CH2 --------------------- >< ----- CH3 --
VET201    QFNGTYRVVSVLPIGHQDWLKGKQFTCKVNNKALPSPIERTISKARGQAHQPSVYVLPPS
VET203    QFNGTYRVVSVLPIGHQDWLKGKQFTCKVNNKALPSPIERTISKARGQAHQPSVYVLPPS
VET206    QSNGTYRVVSVLPIGHQDWLSGKQFKCKVNNKALPSPIEEIISKTPGQAHQPNVYVLPPS
VET200    QSNGTYRVVSVLPIGHQDWLSGKQFKCKVNNKALPSPIEEIISKTPGQAHQPNVYVLPPS
VET205    QFNGTYRVVSVLPIGHQDWLKGKQFTCKVNNKALPSPIERTISKARGQAHQPSVYVLPPS
Identity  * ******************.****.************. ***: ****** *******

Domains   ---------------------- CH3 -------------------------------
VET201    REELSKNTVSLTCLIKDFFPPDIDVEWQSNGQQEPESKYRTTPPQLDEDGSYFLYSKLSV
VET203    REELSKNTVSLTCLIKDFFPPDIDVEWQSNGQQEPESKYRTTPPQLDEDGSYFLYSKLSV
VET206    RDEMSKNTVTLTCLVKDFFPPEIDVEWQSNGQQEPESKYRMTPPQLDEDGSYFLYSKLSV
VET200    RDEMSKNTVTLTCLVKDFFPPEIDVEWQSNGQQEPESKYRMTPPQLDEDGSYFLYSKLSV
VET205    REELSKNTVSLTCLIKDFFPPDIDVEWQSNGQQEPESKYRTTPPQLDEDGSYFLYSKLSV
Identity  *:*:*****:****:******:******:******************* ******************

Domains   ------------- CH3 -------------->
VET201    DKSRWQRGDTFICAVMHEALHNHYTQKSLSHSPGK
VET203    DKSRWQRGDTFICAVMHEALHNHYTQKSLSHSPGK
VET206    DKSRWQRGDTFICAVMHEALHNHYTQKSLSHSPGK
VET200    DKSRWQRGDTFICAVMHEALHNHYTQKSLSHSPGK
VET205    DKSRWQRGDTFICAVMHESLHNHYTQKSLSHSPGK
Identity  ******************:****************
```

The amino acid sequence of the constant domain regions of kappa light chain isolated from canine PBMC samples is listed below.

SEQ ID NO: 8
NDAQPAVYLFQPSPDQLHTGSASVVCLLNSFYPKDINVKWKVDGVIQDTG

IQESVTEQDKDSTYSLSSTLTMSSTEYLSHELYSCEITHKSLPSTLIKSF

QRSECQRVD

The amino acid sequence of the constant domain regions of lambda light chain isolated from canine PBMC samples is listed below.

SEQ ID NO: 9
GQPKASPSVTLFPPSSEELGANKATLVCLISDFYPSGVTVAWKADGSPIT

QGVETTKPSKQSNNKYAASSYLSLTPDKWKSHSSFSCLVTHEGSTVEKKV

APAECS

Recombinant constant domain regions were cloned together with a variable domain and subcloned into pcDNA3 (Invitrogen). After transfection into mammalian cells, the recombinant polypeptides were released into the supernatants. Supernatants were used to test the binding to polypeptides. The soluble recombinant proteins were either purified from the supernatant or used directly for the testing of binding to Fc receptors or alteration of functions in cell assays.

III. Prevalence and Homology of Heavy Constant Domain Regions Sequences.

Analysis of the heavy chain constant domains described herein showed that homology among the constant domains ranged from 81 to 100% and from 89 to 99% at amino acid and nucleotide sequence levels, respectively. Interestingly, the hinge region displayed great variability in composition and in length. Among all of the isolated sequences, VET203 and VET201 were the most frequent sequences and accounted for 53% and 20% of the sequences, respectively. Although their nucleotide sequences exhibited differences, the amino acid sequence of VET202, VET203, and VET204 was identical.

Example 3

Cloning of the Feline Constant Domain Regions

Heavy chain and light chain constant domain sequences from cat were cloned from a cDNA library isolated from spleen tissues. The regions or fragment thereof were amplified by PCR using the primers listed below. The PCR reactions were as follows: 1 µl cDNA, 1 µl forward primer at 20-40 µM, 1 µl reverse primer at 20-40 µM, 16.5 µl H$_2$O, 1 µl polymerase Platinum® Pfx DNA (Invitrogen), and 12.5 µl GoTaq® Green Master Mix (Promega). The samples were denatured at 94° C. for 5 min followed by amplifications for 35 cycles (94° C. for 30 s, 52° C. for 1 min, 72° C. for 1 min). The PCR products were cloned into pJET (Fermentas) or pcDNA 3.1 (Invitrogen) and sequenced to verify PCR specificity.

| Region for Amplification | Primer Designation | Primer Sequence |
|---|---|---|
| HC Constant Domain Full Length | HC-Cat-Forward (SEQ ID NO 22) | 5'-GCTAGCACCACGGCCCCATCGGTG-3' |
| | HC-Cat-Reverse (SEQ ID NO 23) | 5'-GGATCCTCATTTACCCGGAGAATGGG-3' |
| Kappa LC Constant Domain Full Length | K-LC-Cat-Forward (SEQ ID NO 24) | 5'-CTCGAGATCAAACGGAGTGATGC-3' |
| | K-LC-Cat-Reverse (SEQ ID NO 25) | 5'-GGATCCCTACTCTCTCTGACACTC-3' |

TABLE 3

Amino acid sequence of the recombinant feline heavy chain constant domains and the recombinant feline kappa light chain constant domain.

SEQ ID VET NO: 10  241
ASTTAPSVFPLAPSCGTTSGATVALA-
CLVLGYFPEPVTVSWNSGALTSGVHTFPAVLQASGLYSLSSMVTVPSSRW
LSDTFTCNVAHPPSDTKVDKTVRKTDHP-
PGPKPCDCPKCPPPEMLGGPSIFIFPPKPKDTLSISRTPEVTCLVVDL
GPDDSDVQITWFVDNTQVYTAKTSPRE-
EQFNSTYRVVSVLPILHQDWLKGKEFKCKVNSKSLPSPIERTISKAKGQ
PHEPQVYVLPPAQEELSRNKVSVTC-
LIKSFHPPDIAVEWEITGQPEPENNYRTTPPQLDSDGTYFVYSKLSVDRSH
WQRGNTYTCSVSHEALHSHHTQKSLTHSPGK

SEQ ID VET NO: 11  242
ASTTAPSVFPLAPSCGTTSGATVALA-
CLVLGYFPEPVTVSWNSGALTSGVRTFPAVLQASGLYSLSSMVTVPSSRW
LSDTFTCNVAHPPSNTKVDKTVRKTDHP-
PGPKPCDCPKCPPPEMLGGPSIFIFPPKPKDTLSISRTPEVTCLVVDL
GPDDSDVQITWFVDNTQVYTAKTSPRE-
EQFNSTYRVVSVLPILHQDWLKGKEFKCKVNSKSLPSPIERTISKAKGQ
PHEPQVYVLPPAQEELSRNKVSVTC-
LIKSFHPPDIAVEWEITGQPEPENNYRTTPPQLDSDGTYFVYSKLSVDRSH
WQRGNTYTCSVSHEALHSHHTQKSLTHSPGK

SEQ ID VET NO: 12  243
ASTTAPSVFPLAPSCGTTSGATVALA-
CLVLGYFPEPVTVSWNSGALTSGVHTFPSVLQASGLYSLSSMVTVPSSRW
LSDTFTCNVAHPPSNTKVDKTVRKTDHP-
PGPKPCDCPKCPPPEMLGGPSIFIFPPKPKDTLSISRTPEVTCLVVDL
GPDDSDVQITWFVDNTQVYTAKTSPRE-
EQFNSTYRVVSVLPILHQDWLKGKEFKCKVNSKSLPSPIERTISKAKGQ
PHEPQVYVLPPAQEELSRNKVSVTC-
LIKSFHPPDIAVEWEITGQPEPENNYRTTPPQLDSDGTYFVYSKLSVDRSH
WQRGNTYTCSVSHEALHSHHTQKSLTHSPGK

SEQ ID VET NO: 13  244
ASTTAPSVFPLAPSCGTTSGATVALA-
CLVLGYFPEPVTVSWNSGALTSGVHTFPSVLQASGLYSLSSMVTVPSSRW
LSDTFTCNVAHPPSNTKVDKTVRKTDHP-
PGPKPCDCPKCPPPEMLGGPSIFIFPPKPKDTLSISRTPEVTCLVVDL
GPDDSDVQITWFVDNTQVYTAKTSPRE-
EQFNSTYRVVSVPPILHQDWLTGKEFKCKVNSKSLPSPIERTISKAKGQ
PHEPQVYVLPPAQEELSRNKVSVTCLI-
EGFYPSDIAVEWEITGQPEPENNYRTTPPQLDSDGTYFVYSKLSVDRSH
WQRGNTYTCSVSHEALHSHHTQKSLTHSPGK

SEQ ID VET NO: 14  245
ASTTAPSVFPLAPSCGTTSGATVALA-
CLVLGYFPEPVTVSWNSGALTSGVHTFPSVLQASGLYSLSSMVTVPSSRW
LSDTFTCNVAHPPSNTKVDKAVRKTDHP-
PGPKPCDCPKCPPPEMLGGPSIFIFPPKPKDTLSISRTPEVTCLVVDL
GPDDSDVQITWFVDNTQVYTAKTSPRE-
EQFNSTYRVVSVLPILHQDWLKGKEFKCKVNSKSLPSPIERTISKDKGQ
PHEPQVYVLPPAQEELSRNKVSVTCLI-
EGFYPSDIAVEWEITGQPEPENNYRTTPPQLDSDGTYFLYSRLSVDRSR
WQRGNTYTCSVSHEALHSHHTQKSLTHSPGK

TABLE 3-continued

Amino acid sequence of the recombinant feline heavy chain constant domains and the recombinant feline kappa light chain constant domain.

| | | |
|---|---|---|
| SEQ ID NO: 15 | VET 246 | ASTTAPSVFPLAPSCGTTSGATVALA-<br>CLVLGYFPEPVTVSWNSGALTSGVHTFPSVLQASGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKDKGQ<br>PHEPQVYVLPPAQEELSRNKVSVTCLI-<br>EGFYPSDIAVEWEITGQPEPENNYRTTPPQLDSDGTYFLYSRLSVDRSR<br>WQRGNTYTCSVSHEALHSHHTQKSLTHSPGK |
| SEQ ID NO: 16 | VET 247 | ASTTAPSVFPLAPSCGTTSGATVALA-<br>CLVLGYFPEPVTVSWNSGALTSGVHTFPSVLQASGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKDKGQ<br>PHEPQVYVLPPAQEELSRNKVSVTCLI-<br>EGFYPSDIAVEWEITGQPEPENNYRTTPPQLDSDGTYFLYSRLSVDRSR<br>WQRGNTYTCPVSHEALHSHHTQKSLTHSPGK |
| SEQ ID NO: 17 | VET 248 | ASTTAPSVFPLAPSCGTTSGATVALA-<br>CLVLGYFPEPVTVSWNSGALTSGVHTFPAVLQPSGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKDKGQ<br>PHEPQVYVLPPAQEELSRNKVSVTCLI-<br>EGFYPSDIAVEWEITGQPEPENNYRTTPPQLDSDGTYFLYSRLSVDRSR<br>WQRGNTYTCSVSHEALHSHHTQKSLTHSPGK |
| SEQ ID NO: 18 | VET 249 | ASTTAPSVFPLAPSCGTTSGATVALA-<br>CLVLGYFPEPVTVSWNSGALTSGVHTFPAVLQASGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKDKGQ<br>PHEPQVYVLPPAQEELSRNKVSVTC-<br>LIKSFHPPDIAVEWEITGQPEPENNYRTTPPQLDSDGTYFVYSKLSVDRSH<br>WQRGNTYTCSVSHEALHSHHTQKSLTHSPGK |
| SEQ ID NO: 19 | VET 250 | ASTTAPSVFPLAPSCGTTSGATVALA-<br>CLVLGYFPEPVTVSWNSGALTSGVHTFPAVLQASGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKAKGQ<br>PHEPQVYVLPPAQEELSRNKVSVTR-<br>LIKSFHPPDIAVEWEITGQPEPENNYRTTPPQLDSDGTYFVYSKLSVDRSH<br>WQRGNTYTCSVSHEALHSHHTQKSLTHSPG |
| SEQ ID NO: 20 | VET 251 | ASTTAPSVFPLAPSCGTTSGATVALA-<br>CLVLGYFPEPVTVSWNSGALTSGVHTFPSVLQASGLYSLSSMVTVPSSRW<br>LSDTFTCNVAHPPSNTKVDKTVRKTDHP-<br>PGPKPCDCPKCPPPEMLGGPSIFIFPPKPKDTLSISRTPEVTCLVVDL<br>GPDDSDVQITWFVDNTQVYTAKTSPRE-<br>EQFNSTYRVVSVLPILHQDWLKGKEFKCKVNSKSLPSPIERTISKDKGQ<br>PHEPQVYVLPPAQEELSRNKVSVTCLI-<br>EGFYPSDIAVEWEITGTAGAREQLPGRPRPSWNSDGTYFLYSRLSVDRS<br>RWQRGNTYTCSVSHEALHSHHTQKSLTHSPGK |
| SEQ ID NO: 21 | VET 131 | RSDAQPSVFLFQPSLDELHTGSA-<br>SIVCILNDFYPKEVNVKWKVDGVVQNKGIQESTTEQNSKDSTYSLSSTLTMSS<br>TEYQSHEKFSCEVTHKSLASTLVKSFNRSECQRE |

Example 4

Construction, Expression and Purification of Recombinant Antibody Variants

I. Construction of Antibody Variants.

Recombinant antibody polypeptides were constructed from isolated canine heavy chain constant domains and from an isolated canine lambda light chain constant domain of the present invention. In order to assess their functions, variable domains were cloned together with the constant domains. The variable regions of this example include the rat anti-human CD52, the sequence of which is described in pdb 1bfo_E and pdb 1bfo_F (Campath-1G, clone YTH 34.5HL, Protein Data Bank proteins (pdb), date of deposition: May 20, 1998). The variable domains were prepared by assembling synthetic oligonucleotides corresponding to the publicly available sequence. Assembled products were then subcloned into an expression vector containing a promoter and the canine heavy chain constant domains and containing the canine lambda light chain constant domain of the present invention. The entire expression cassette included the human cytomegalovirus immediate-early (CMV) promoter, a kozak sequence and signal peptide sequence immediately upstream of the coding sequence and in frame with the variable region of both the light and heavy chains to direct the resulting antibody product towards the secretory pathway.

II. Expression, Purification and Quantitation of Antibody Variants.

The vectors containing the recombinant heavy chains and the recombinant light chain were transformed into *E. coli* (DH5a) chemically competent *E. coli* cells (Lucigen), grown in Luria Broth (LB) media and stocked in glycerol. Large scale plasmid DNA was prepared using the Zyppy™ Plasmid Maxiprep Kit as described by the manufacturer (Zymo Research Corp.). The antibody variants were transiently expressed in the human embryonic kidney cell line 293F (Invitrogen) under serum-free conditions. The heavy chain (VET200 series) and light chain (VET100 series) expression vectors were co-transfected using 293fectin (Invitrogen) and grown in 293F-FreeStyle culture medium (Invitrogen). The transfected 293 cultures expressed approximately 3-15 mg/L of recombinant antibody. Binding assays were performed with supernatants or with recombinant antibodies purified from supernatants.

The antibody titer was determined using a quantitative ELISA. Plates were coated with 100 ul/well at 37° C. for 1 hour with rabbit anti-dog IgG (H+L) antibody (Jackson Immuno-Research) diluted 1:100 in carbonate buffer (100 mM $NaHCO_3$, 33.6 mM $Na_2CO_3$, pH 9.5). The plates were washed three times with TBS-T (50 mM Tris, 0.14 M NaCl, 0.05% tween-20, pH 8.0) and blocked with 200 ul/well TBS/BSA (50 mM Tris, 0.14 M NaCl, 1% BSA, pH 8.0) for 1 hour at 37° C. The standard was prepared by diluting the reference antibody (Jackson Immuno-Research, Dog Gamma Globulin 10.0 mg) in TBS-T/BSA (TBS-T, 1% BSA) in a range of concentration from 0 to 500 ng/ml. After washing the plates twice with TBS-T, standard/samples preparation was added to each well and incubated at 37° C. for 1 hour. The plates were then washed 3× with TBS-T and incubated for 1 hour at 37° C. with HRP-rabbit anti-dog IgG antibody (Peroxidase Rabbit Anti-Dog IgG (H+L) Jackson Immuno-Research) diluted 1:20,000 in TBS-T/BSA. The plates were washed twice with TBS-T and developed using 100 ul/well of TMB substrate. The reaction was stopped with 1M $H_2SO_4$ and the OD was measured at 450 nm. The standard curve was fitted using a four parameter equation and used to calculate the antibody concentration in the samples.

Antibodies were purified from culture supernatants using protein A affinity chromatography. Supernatants were diluted 1:1 with Binding Buffer (Pierce) and passed over a gravity-flow column (GE Healthcare), equilibrated with 20 resin-bed volumes of Binding Buffer. The antibody retained on the column was washed with 15 ml of binding buffer, eluted with low pH elution buffer (Pierce) and collected in 1 ml fractions containing 100 ul of Binding Buffer to neutralize the pH. Fractions with absorbance (280 nm)>0.1 were desalted using desalting columns (Pierce).

Example 4

Effector Functions of Antibody Variants

I. ADCC-Mediated Properties.
ADCC Assay:

Fresh canine PBMC from normal donors and diseased donors are plated in wells at concentrations of $5 \times 10^5$, $2.5 \times 10^5$, and $1.25 \times 10^5$ cells in 50 µl medium per well to assure effector to target ratios of 100:1, 50:1, and 25:1 with the addition of 5,000 target cells to each well. Each condition is performed in triplicate and the plates are incubated for 3 days at 37° C. in a 5% $CO_2$ humidified atmosphere. After 4 days, 5,000 viable $^{51}$Cr-labeled tumor cells are added to each well as targets. The cells are $^{51}$Cr-labeled by incubation with 250 µCi of $^{51}$Cr for 2 h at 37° C., then washed and resuspended in medium prior to addition to the plates. Then, 50 µl of mAb is added to the wells. Control wells, performed in triplicates contain radiolabeled tumor cells alone to determine spontaneous release of the radiolabel. Maximal release of $^{51}$Cr from tumor cells is established by culturing targets with 150 µl of 1% detergent. Effector and target cells are co-cultured for 16 h, at which time cell-free supernatants are harvested Released radiolabel is determined with a gamma counter. The % cytotoxicity is determined using the formula: (Experimental cpm count−Spontaneous cpm count)/(Maximal cpm count−Spontaneous cpm count). Spontaneous release represents the radioactivity of culture supernatants from the target cells alone, maximal count measures the radioactivity of supernatants from target cells lysed with 1% detergent, and experimental release determines the radioactivity measured in supernatants from wells containing targets plus effector cells.

In the present study, the antibody variants were compared with respect to ADCC functions. Antibody variants with improved as well as diminished ADCC functions were identified.

The ability of the recombinant antibody variants to promote cell killing of a tumor cell line via ADCC was assessed using cancer target cells and Peripheral Blood Mononuclear cells (PBMC) as effectors cells. PBMC were isolated from blood samples obtained from venous blood with citrate of healthy adult dogs (Innovative Research) by separation over a Ficoll-Paque Plus (Endotoxin Tested, Pharmacia Biotech, Uppsala, Sweden) discontinuous density gradient and centrifuged at 800×rpm at room temperature without brake. The isolated cells were washed twice in saline buffer and resuspended in serum-free medium. Target cells (canine lymphoma cell line) were seeded at $20 \times 10^3$ per well and incubated with the antibody variants (0.5 µl/ml), a positive control (anti-human CD52 antibody), and a canine isotype control IgG (Jackson Immuno-Research, Dog Gamma Globulin 10.0 mg) for 30 min. Afterwards, the effector cells were added in varying effector to target ratios of 0:1, 2:1, and 10:1. Each condition was performed in triplicate and the plates were incubated for 16 h at 37° C. in a 5% $CO_2$ humidified atmosphere. A colorimetric-based lactate dehydrogenase (LDH) assay (CytoTox 96; Promega) was used and lysis was calculated according to manufacturer's instructions using the following formula: % Lysis=(Experimental−Effector Spontaneous−Target Spontaneous)/(Target Maximal−Target Spontaneous). Spontaneous represents the LDH level of culture supernatants from the target cells alone or effector cells alone, maximal values measure the LDH level of supernatants from target cells or effector cells lysed with detergent, and experimental values is measured in supernatants from wells containing targets plus effector cells.

Typical results are reported in Table 4. The results of Table 4, with data expressed in percentage lysis, evidence ADCC-mediated killing of tumor cells by the positive control antibody and by the antibody variants. Certain variants were substantially more effective at mediating ADCC than others.

TABLE 4

Antibody variants tested for ADCC-mediated functions.

| Variant | Ratio 0:1 | Ratio 2:1 | Ratio 5:1 |
|---|---|---|---|
| VET 200 | 18.5 | 59.2 | 102.2 |
| VET 201 | 10.3 | 80.5 | 152.7 |
| VET 203 | 6.0 | 59.1 | 142.6 |
| VET 205 | 5.4 | 69.0 | 94.5 |
| VET 206 | 16.3 | 39.4 | 125.5 |

TABLE 4-continued

Antibody variants tested for ADCC-mediated functions.

| Variant | Ratio 0:1 | Ratio 2:1 | Ratio 5:1 |
|---|---|---|---|
| Isotype | 4.1 | 17.3 | 58.8 |
| Positive Control | 14.7 | 50.1 | 158.0 |

II. Complement-Mediated Properties.

In the present study, the antibody variants were compared with respect to CDC functions. Antibody variants with improved as well as diminished CDC functions were identified.

The ability of the recombinant antibodies to promote cell killing of a tumor cell line via complement was assessed. Serum complement from dog or guinea pig (Innovative Research) was used. In a typical assay, target cells (canine lymphoma cell line) were seeded at $20 \times 10^3$ per well and incubated with the antibody variants (0.5 µl/ml), a positive control (anti-human CD52 antibody), and a canine isotype control IgG (Jackson Immuno-Research, Dog Gamma Globulin 10.0 mg) for 30 min. Afterwards, the complement diluted in RPMI 1640 was added in varying complement to target ratios of 0:1, 2:1, and 5:1. The mixture was incubated for 16 h at 37° C. in a 5% $CO_2$. A colorimetric-based lactate dehydrogenase (LDH) assay (CytoTox 96; Promega) that measures the level of cytosolic LDH release upon lysis of cells was used and the average absorbance of triplicates was used to calculate the percentage of cell lysis. Cell lysis was calculated according to manufacturer's instructions using the following formula: % Lysis=(Experimental−Complement Spontaneous−Target Spontaneous)/(Target Maximal−Target Spontaneous). Spontaneous represents the LDH level of culture supernatants from the target cells alone or complement alone, maximal values measure the LDH level of supernatants from target cells or complement lysed with detergent, and experimental values is measured in supernatants from wells containing targets plus complement.

Typical results are reported in Table 5. The results of Table 5, with data expressed in percentage lysis, evidence CDC-mediated killing of tumor cells by the positive control antibody and by the antibody variants. Certain variants were substantially more effective at mediating CDC than others.

TABLE 5

Antibody variants tested for CDC-mediated functions.

| Variant | Ratio 0:1 | Ratio 2:1 | Ratio 5:1 |
|---|---|---|---|
| VET 200 | 14.9 | 48.1 | 77.7 |
| VET 201 | 13.0 | 21.5 | 73.9 |
| VET 203 | 9.8 | 19.5 | 47.9 |
| VET 205 | 7.2 | 20.2 | 61.6 |
| VET 206 | 7.2 | 13.6 | 35.9 |
| Isotype | 2.1 | 10.6 | 25.2 |
| Positive Control | 12.6 | 30.4 | 74.4 |

Example 5

Biophysical Properties of Antibody Variants

The antibody variants of the invention were tested for thermal stability. The variants were compared in a thermal challenge assay which can be used to determine (1) the temperature at which 50% of the variant retain their antigen binding activity following a thermal challenge event and/or (2) the temperature at which 50% of the variant remain soluble. The numerical value corresponding to this temperature is referred to as the "T50" or "TM" value and the units are in ° C. Noteworthy, the "TM" determined in this assay is an approximate midpoint temperature of thermal denaturation and should not necessarily be construed as being equivalent to biophysically derived TM values.

The approximate TM for the variants was determined. The only difference between all the tested variants was the heavy chain constant domains.

Each variant was assessed in triplicate using a thermal challenge assay. In this assay, the variants were subjected to a range of temperatures that encompass the thermal transition temperature of canine non recombinant IgG. Thermocycler machines capable of generating stable thermal gradients were used to treat the samples. An aliquot (10 µg/mL) of purified antibody variants and of a canine isotype control IgG (Jackson Immuno-Research, Dog Gamma Globulin 10.0 mg) was distributed into PCR microtubes and incubated for 10 min at temperatures between 50 and 85° C., before rapid cooling on ice. After thermal challenge of the variants, the samples were centrifuged to remove aggregated material. Subsequently, the residual concentration of antibody in the supernatant was measured using the quantitative ELISA assay described in Example 3. The results were analyzed using Prism 4 software (GraphPad Software) using a sigmoidal dose response with variable slope as the model.

As shown in Table 6, the variants exhibited a TM within a range of 65° C.-69° C. The variant VET 203 containing the heavy chain constant domain from the most prevalent form isolated from a cDNA library made from canine PBMC or canine spleen exhibited the highest TM. The amount of soluble antibody remaining after thermal challenge at 75° C. varied amongst the variants, with the most prevalent forms having the highest residual level (Table 6).

TABLE 6

TM of Antibody Variants.

| Antibody | Canine IgG | VET200 | VET201 | VET203 | VET205 | VET206 |
|---|---|---|---|---|---|---|
| TM (° C.) | 67.89 | 65.92 | 67.64 | 69.01 | 66.21 | 65.92 |
| Residual IgG (%) | 29.18 | 27.59 | 41.48 | 44.01 | 44.21 | 22.71 |

Alternative combinations and variations of the examples provided will become apparent based on this disclosure. It is not possible to provide specific examples for all of the many possible combinations and variations of the embodiments described, but such combinations and variations may be claims that eventually issue.

The invention claimed is:

1. A recombinant protein comprising
   a. a binding domain, or a fragment thereof, that specifically binds to an epitope; the binding domain comprising (i) a non-canine antibody hypervariable region or an epitope-binding fragment thereof, or (ii) a soluble receptor binding domain or an epitope-binding fragment thereof; and
   b. an effector domain that provides ADCC and/or CDC effector function to the recombinant protein; the effector domain comprising a constant domain region; wherein the constant domain region comprises SEQ ID NO: 2.

2. The recombinant protein of claim 1 which is a member of the immunoglobulin superfamily comprising an Ig fold.

3. The recombinant protein of claim 1, wherein the binding domain comprises an antibody variable region.

4. The recombinant protein of claim 1, wherein the epitope is selected from the group consisting of: a receptor, a growth factor, and a cytokine.

5. The recombinant protein of claim 1, wherein the effector domain binds to an FcR.

6. The recombinant protein of claim 1, wherein the recombinant protein has increased ADCC effector function relative to dog gamma globulin.

7. The recombinant protein of claim 1, wherein the recombinant protein has increased CDC effector function relative to dog gamma globulin.

8. The recombinant protein of claim 1, wherein the recombinant protein exhibits a TM of at least about the TM of dog gamma globulin.

9. The recombinant protein of claim 1, wherein the effector domain further comprises a constant domain region of a kappa light chain comprising the sequence set forth in SEQ ID NO:8.

10. The recombinant protein of claim 1, wherein the effector domain further comprises a constant domain region of a lambda light chain comprising the sequence set forth in SEQ ID NO:9.

11. A recombinant protein according to claim 1 wherein the binding domain comprises hypervariable regions from an antibody from a species other than the companion animal.

12. A recombinant protein according to claim 11 which is a heterochimeric antibody.

13. A pharmaceutical composition comprising the recombinant protein according to claim 1, in combination or association with a pharmaceutically acceptable diluent of carrier.

14. A recombinant protein comprising SEQ ID NO: 2.

* * * * *